(12) United States Patent
Burkinshaw et al.

(10) Patent No.: US 8,357,147 B2
(45) Date of Patent: Jan. 22, 2013

(54) METHOD FOR REPAIRING INTERVERTEBRAL DISCS

(75) Inventors: Brian D. Burkinshaw, Pflugerville, TX (US); John L. Wheeler, Austin, TX (US); James B. Rogan, Austin, TX (US); Steven I. Whitlock, Austin, TX (US)

(73) Assignee: Spinal Restoration, Inc., Austin, TX (US)

( * ) Notice: Subject to any disclaimer, the term of this patent is extended or adjusted under 35 U.S.C. 154(b) by 698 days.

(21) Appl. No.: 11/707,769

(22) Filed: Feb. 16, 2007

(65) Prior Publication Data
US 2008/0103564 A1    May 1, 2008

Related U.S. Application Data

(63) Continuation-in-part of application No. 11/650,306, filed on Jan. 5, 2007, which is a continuation-in-part of application No. 11/205,760, filed on Aug. 17, 2005, and a continuation-in-part of application No. 11/205,784, filed on Aug. 17, 2005, and a continuation-in-part of application No. 11/205,775, filed on Aug. 17, 2005, now Pat. No. 7,597,687, application No. 11/707,769, which is a continuation-in-part of application No. 11/650,398, filed on Jan. 5, 2007, which is a continuation-in-part of application No. 11/205,760, and a continuation-in-part of application No. 11/205,784, and a continuation-in-part of application No. 11/205,775.

(60) Provisional application No. 60/623,600, filed on Oct. 29, 2004, provisional application No. 60/764,019, filed on Feb. 1, 2006, provisional application No. 60/854,413, filed on Oct. 24, 2006.

(51) Int. Cl.
*A61B 18/04* (2006.01)

(52) U.S. Cl. ............... 606/27; 604/57; 604/58; 604/59; 604/60; 604/61; 604/63; 604/64; 604/82; 604/83; 604/84; 604/85; 604/86; 604/87; 604/88; 604/89; 604/90; 604/91; 604/92; 604/181; 604/187; 604/275; 604/276; 604/277; 604/278; 604/279

(58) Field of Classification Search ............. 604/57–64, 604/82–92, 181, 187, 275–279
See application file for complete search history.

(56) References Cited

U.S. PATENT DOCUMENTS 4,872,483 A * 10/1989 Shah ........................... 137/557

(Continued)

OTHER PUBLICATIONS

Dictionary.com. "Through | Define Through at Dictionary.com". Accessed online Oct. 1, 2010. http://www.dictionary.com.*

(Continued)

*Primary Examiner* — Nicholas Lucchesi
*Assistant Examiner* — Scott Medway
(74) *Attorney, Agent, or Firm* — O'Keefe, Egan, Peterman & Enders LLP

(57) ABSTRACT

A method of repairing a defect in an annulus fibrosus of an intervertebral disc, without excising the entire nucleus pulposus of the disc. The method includes inserting an introducer needle through the annulus fibrosus by puncturing the annulus fibrosus with the introducer needle, injecting an in situ curable, bio-compatible polymerizable or polymeric material composition into the disc through the introducer needle directly or indirectly so that the in situ curable composition contacts a defect in the annulus fibrosus; and curing said material in situ.

27 Claims, 24 Drawing Sheets

U.S. PATENT DOCUMENTS

| | | | | |
|---|---|---|---|---|
| 4,979,942 | A | | 12/1990 | Wolf et al. .................. 604/83 |
| 5,080,648 | A | * | 1/1992 | D'Antonio .................. 604/72 |
| 5,259,838 | A | * | 11/1993 | Taylor et al. ............... 604/97.03 |
| 6,428,576 | B1 | * | 8/2002 | Haldimann ................ 623/17.16 |
| 6,534,591 | B2 | * | 3/2003 | Rhee et al. ................ 525/54.1 |
| 6,723,095 | B2 | * | 4/2004 | Hammerslag ................ 606/60 |
| 7,001,431 | B2 | * | 2/2006 | Bao et al. .................. 623/17.12 |
| 7,077,865 | B2 | * | 7/2006 | Bao et al. .................. 623/17.12 |
| 7,279,001 | B2 | * | 10/2007 | Addis et al. ................ 606/214 |
| 7,449,019 | B2 | * | 11/2008 | Uchida et al. ............... 606/27 |
| 2002/0198599 | A1 | | 12/2002 | Haldimann ................ 623/17.16 |
| 2006/0004326 | A1 | | 1/2006 | Collins et al. ................ 604/57 |
| 2006/0106364 | A1 | | 5/2006 | Whitlock et al. ............ 604/506 |

OTHER PUBLICATIONS

PCT/US08/00253 filed Feb. 15, 2008, "Search Report," Jul. 17, 2008.

* cited by examiner

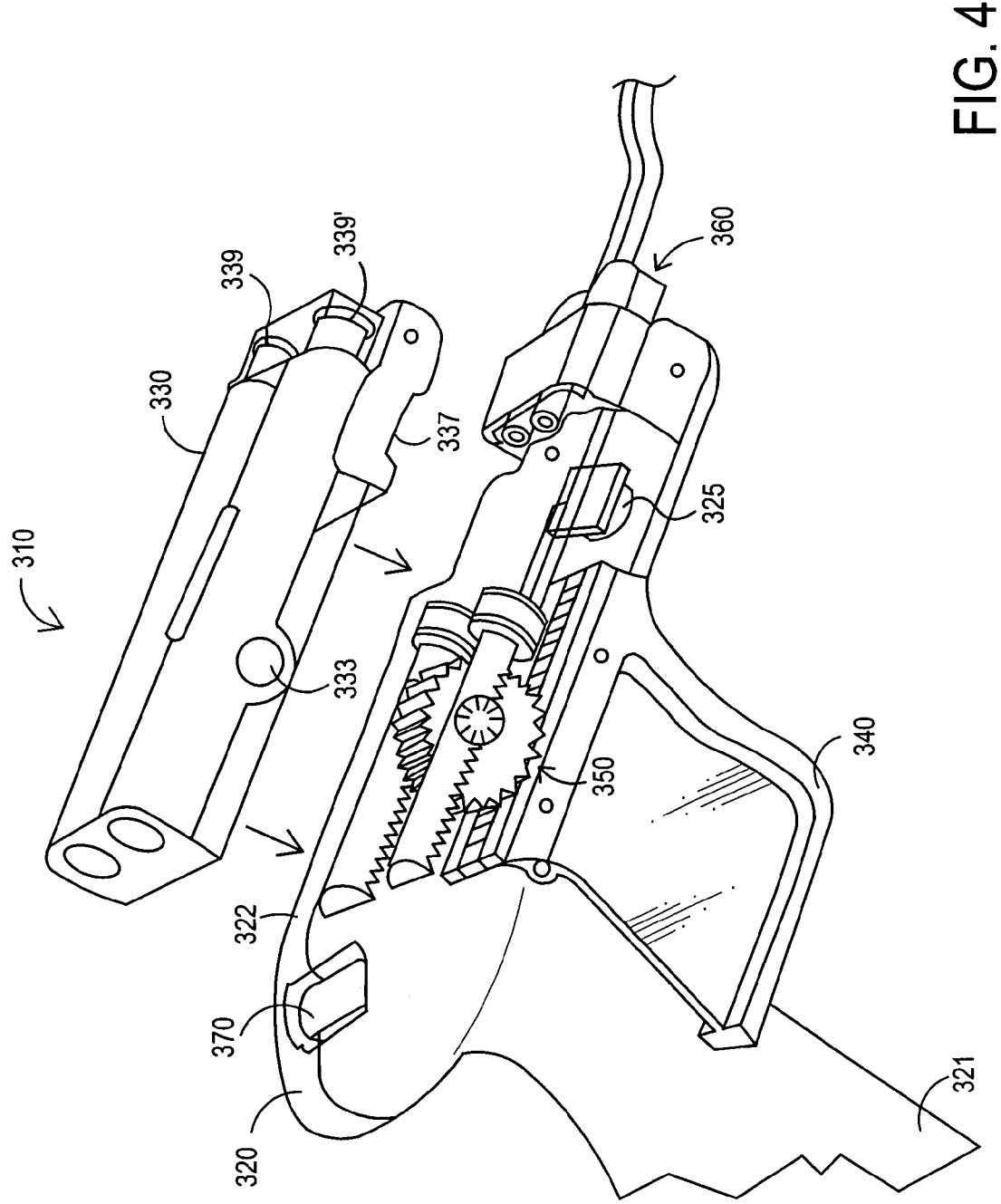

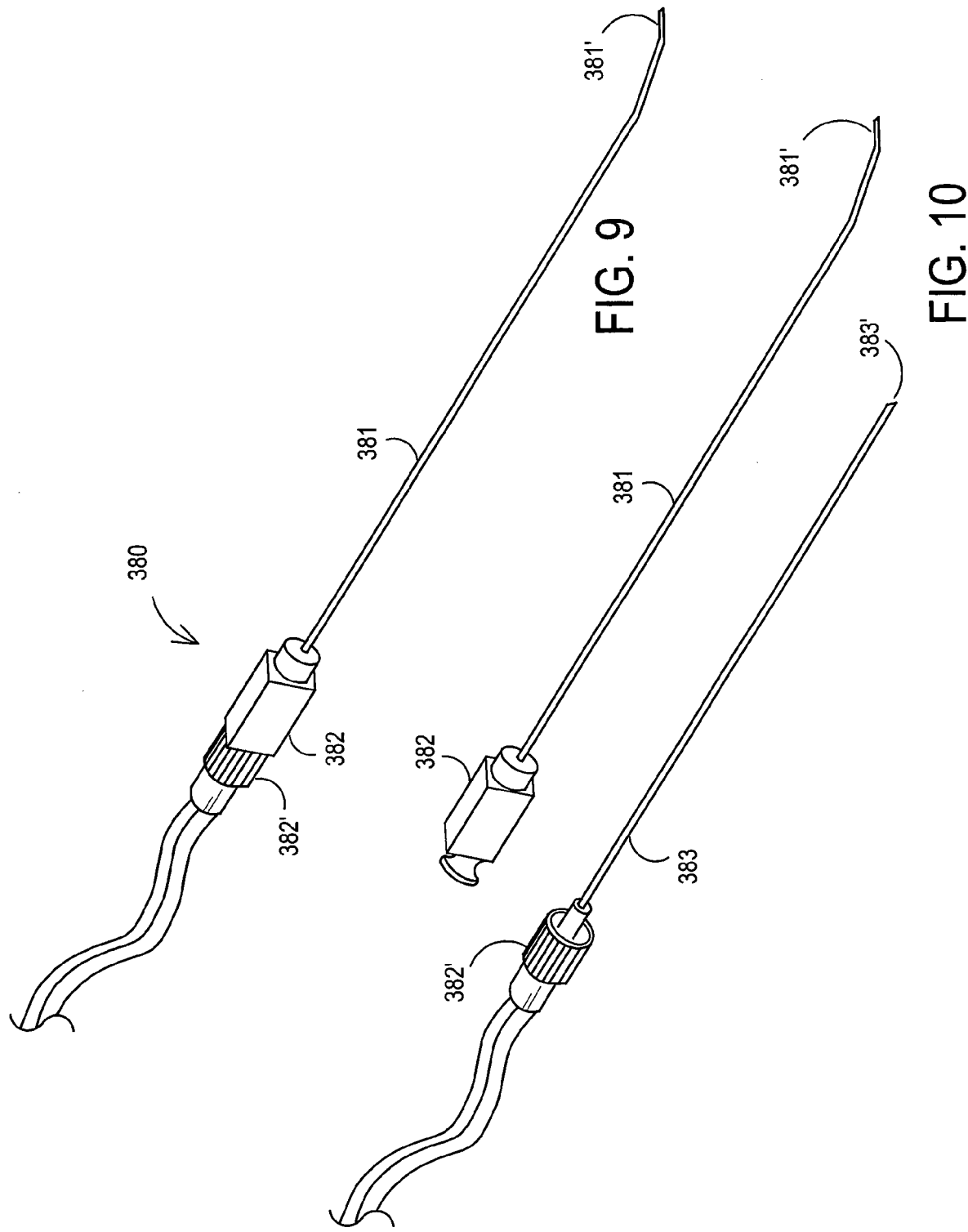

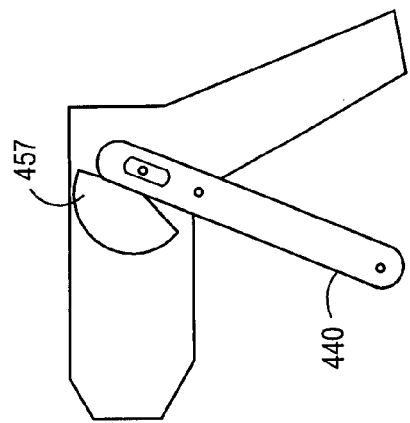
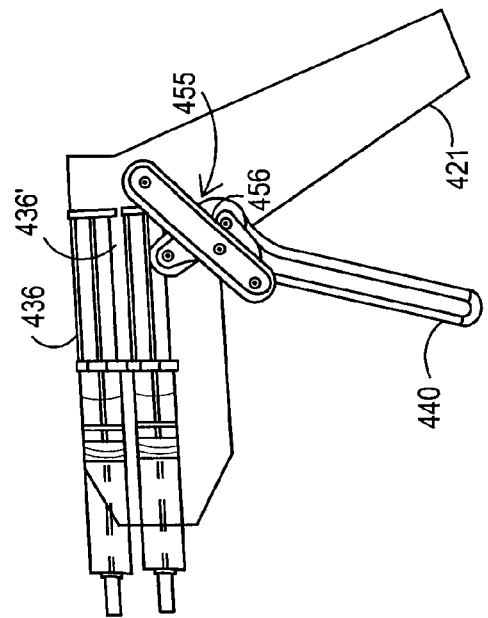
FIG. 19A
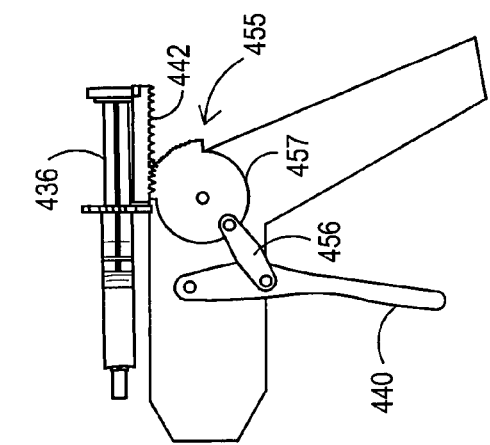
FIG. 19B
FIG. 19C

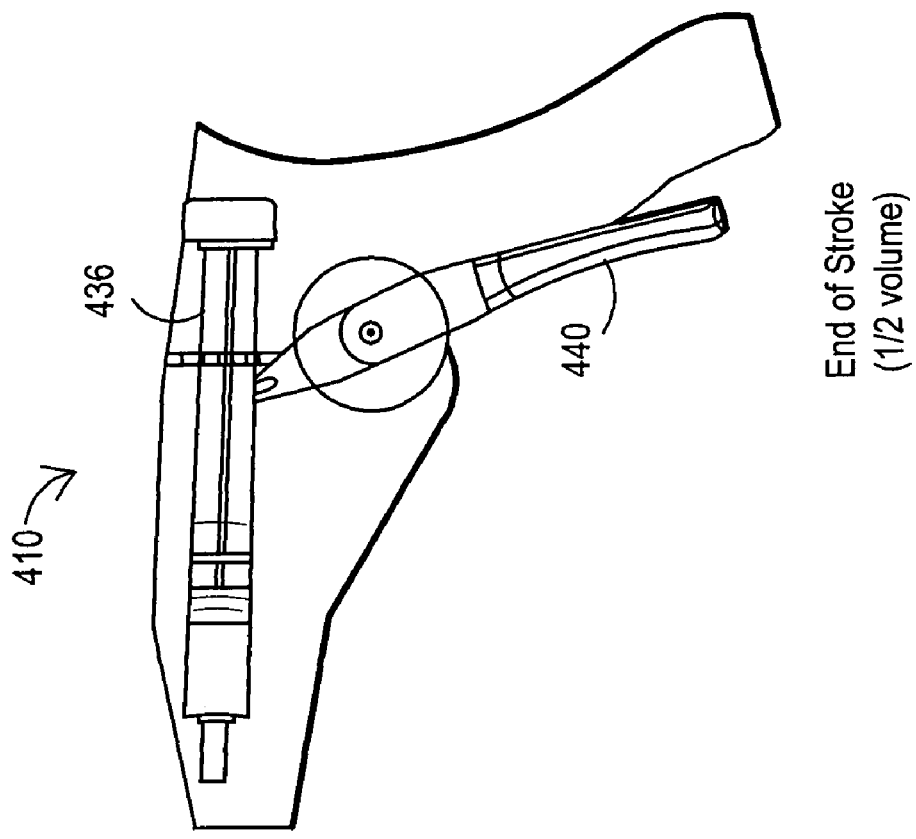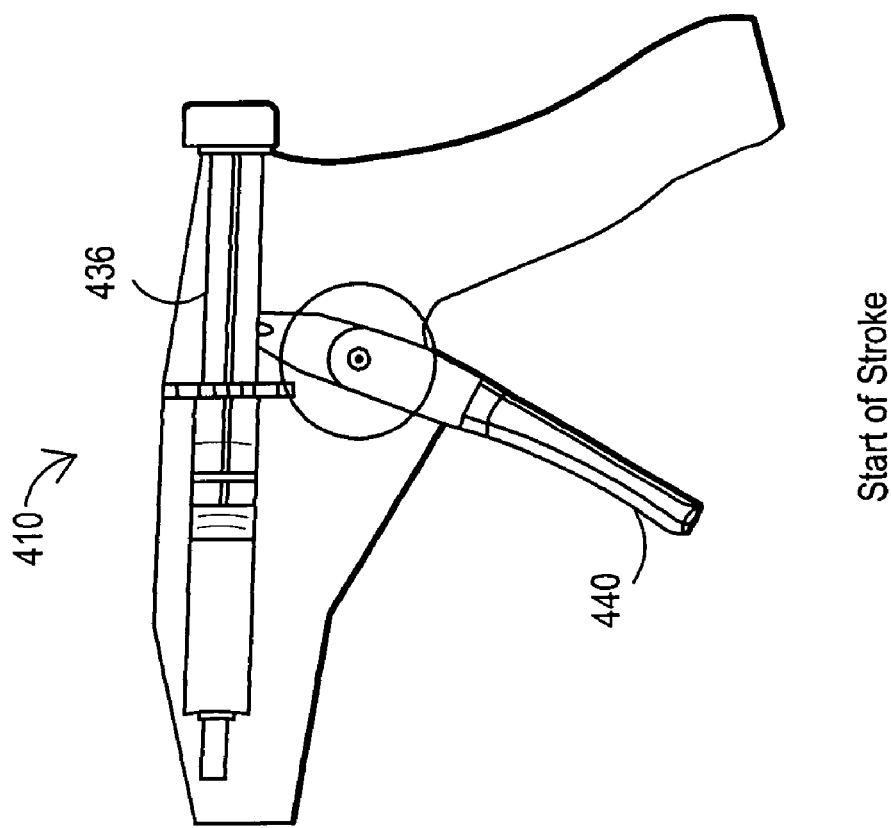
FIG. 20

METHOD FOR REPAIRING INTERVERTEBRAL DISCS

This application is a continuation-in-part of copending application Ser. No. 11/650,306, filed Jan. 5, 2007, which claims priority to U.S. provisional application No. 60/623,600, filed Oct. 29, 2004 and which is a continuation-in-part of U.S. application Ser. No. 11/205,760, filed Aug. 17, 2005, of U.S. application Ser. No. 11/205,784, filed Aug. 17, 2005, and of U.S. application Ser. No. 11/205,775, filed Aug. 17, 2005, now U.S. Pat. No. 7,597,687, and to U.S. provisional application No. 60/764,019, filed Feb. 1, 2006, and to U.S. provisional application No. 60/854,413, filed Oct. 24, 2006; this application is also a continuation-in-part of application Ser. No. 11/650,398, filed Jan. 5, 2007, which claims priority to U.S. provisional application No. 60/623,600, filed Oct. 29, 2004 and which is a continuation-in-part of U.S. application Ser. No. 11/205,760, filed Aug. 17, 2005, of U.S. application Ser. No. 11/205,784, filed Aug. 17, 2005, and of U.S. application Ser. No. 11/205,775, filed Aug. 17, 2005, now U.S. Pat. No. 7,597,687, and to U.S. provisional application No. 60/764,020, filed Feb. 1, 2006, and to U.S. provisional application No. 60/854,413, filed Oct. 24, 2006; all of which are incorporated herein by reference.

BACKGROUND OF THE INVENTION

The present invention is directed to a method for repairing tissue defects in intervertebral discs, including repair of a spinal joint and repair of fissures in the annulus fibrosus. It more particularly is concerned with repairing the portion of an intervertebral disc that has been subject to damage, such as herniation, resulting from natural degeneration, and/or trauma, as well as to repairing that portion of an intervertebral disc remaining after the performance of a partial discectomy intervention. Such discectomies are conventionally performed to treat a severe hernia of an intervertebral disc.

The term 'Disc Herniation' (or 'disc prolapse' as they use in Europe) is a broad and general term that includes three specific types of disc lesion, which are classified based on the degree of disc disruption and posterior longitudinal ligament (PLL) disruption. The three main classifications of disc herniation are Protrusion (aka: contained herniation or sub-ligamentous herniation), Extrusion (aka: non-contained herniation, or trans-ligamentous herniation) and Sequestration (aka: free fragment). A disc hernia is a radial rupture of the annulus fibrosus of the intervertebral disc that may be accompanied by a protrusion (sometimes a very large protrusion—also referred to as an Extrusion) of the annulus fibrosus and/or by an extrusion of disc material through the rupture in the annulus fibrosus. The rupture of the annulus fibrosus is often accompanied by a compression of the spinal canal and pressure on the nerve roots that pass through the disc protrusion or extrusion. This usually leads to strong and progressive pain that emanates from the compromised segment of the spine. This condition may require a surgical intervention. Disc Sequestration represents the end-of-the-line for the cycle of disc herniation. This condition manifests when a large 'fragment' of nuclear material has detached itself from the main body of the extrusion and is loose in the epidural space. This will typically result in severe compression of the traversing nerve root, the exiting nerve root, and the lateral aspect of the Thecal Sac. Sequestration (aka: sequester, free-fragment) may be excruciatingly painful (back and leg pain—sciatica) and, if centrally located, may occasionally cause the patient to lose control of their bowl and bladder function, i.e., Cauda Equina Syndrome, which is considered a medical emergency.

Patients with a symptomatic disc hernia, and indication for a surgical intervention at the disc, normally undergo a partial or total discectomy operation. In a partial discectomy, protruding annulus disc material and a portion of the nucleus pulposus of the disc are removed. The resulting reduction in the volume of disc material within the epidural space leads to decreased pressure on the compressed nerve roots and/or the spinal cord, respectively. Without repair, the radial rupture defect in the annulus fibrosus will remain and will not close, at least it will not close in a relatively short time. Without repair, a considerable risk of post-discectomy complications, such as a re-herniation of the disc, will remain.

A successful discectomy intervention will result in lasting pain relief for the patient. However, it has been shown that severe post-discectomy complications may occur in about 6-16% of all surgical interventions. These are often caused by events such as a re-herniation of the disc, extensive epidural scar formation or vascularization and nerve ingrowth into the defect in the annulus fibrosus.

The cells of the nucleus pulposus produce cytokines and inflammatory mediators, such as nitric oxide, that have been shown to be responsible for nerve root irritation and sensitization that can lead to severe radicular pain. In a post-discectomy situation, without repair of the annulus fibrosus, nucleus pulposus material may migrate into the epidural space and/or nucleus pulposus-derived cytokines and inflammatory mediators may diffuse into the epidural space through the annulotomy site. Both events may result in post-discectomy complications such as persistent nerve root pain and/or irritation of nociceptors in the outer ⅓ of the disc annulus.

As a side effect of the volume reduction that is attendant upon a discectomy intervention, the intervertebral disc height, and thus the vertical distance between adjacent vertebral bodies, will be reduced. The decreased intervertebral disc height may be one of the reasons for a re-herniation of the disc. Further, the reduction in intervertebral disc height has been reported to lead to an accelerated mono-segmental degeneration of the annulus fibrosus or of the facet joints of the affected spinal segment.

Research is ongoing with respect to mechanical disc replacements, hydrogel implant replacements and in situ curable polyurethane disc replacements.

Recently, fibrin sealant that included a corticosteroid was used to treat disc problems such as fissures in the annulus fibrosus. In this regard, U.S. Pat. No. 6,468,527 discloses that the composition was injected into a disc (an intra-discal injection) to treat disc problems. In U.S. Pat. No. 6,468,527 the fibrin sealant is injected by inserting an introducer needle into disc, inserting a second needle through the introducer needle that is connected to a dual barrel syringe, and then injecting the fibrinogen and thrombin into the disc. The fibrinogen and thrombin begin mixing at the "Y" connection and throughout the length of the needle.

The inventors herein have identified that a need exists for alternative processes of repairing the spinal joints including the annulus using materials other than fibrin sealant.

SUMMARY OF THE INVENTION

This invention provides a solution to one or more of the problems and/or deficiencies identified above.

This invention, in one broad respect, provides a process for repairing a spinal joint including the annulus fibrosus by injecting a polymerizable composition into the disc.

The in-situ curable sealant material provides the surgeon with means for repairing the annulus fibrosus by injecting the in-situ curable composition into the disc so that the composition flows out into and at least partially seals fissures in the annulus to thereby delimit material from the nucleus pulposus from flowing through the fissures to the outside of the disc. The injection of the curable composition into the disc has been determined to be superior to the deposition of curable composition disclosed in U.S. Pat. No. 6,428,576, wherein curable composition was not injected into the disc such that composition flowed outward from the center of the disc to fill voids and fissures in the annulus. Thus, in accordance with this invention, by the superior process of injection disclosed herein, the annulus is at least partially sealed to thereby reduce or eliminate migration of nucleus pulposus cells into the epidural space, and to prevent, by sealing the annulus, diffusion of nucleus pulposus-derived cytokines and inflammatory mediators into the epidural space through the annulotomy site. The thus resulting prevention of contact between nucleus pulposus cells, and its cytokines or inflammatory mediators, with nerve roots after discectomy is another object of the invention and will assist to minimize nucleus pulposus-induced nerve root injury and nerve root pain. Likewise, the present invention contemplates injection of the curable composition in other spinal joints where a fibrous capsule surrounds a core.

In one broad respect, this invention is a method of repairing a defect in an annulus fibrosus of an intervertebral disc, without excising the entire nucleus pulposus of the disc, comprising: inserting an introducer needle through the annulus fibrosus by puncturing the annulus fibrosus with the introducer needle, injecting an in situ curable, bio-compatible polymerizable or polymeric material composition into the disc through the introducer needle directly or indirectly so that the in situ curable composition contacts a defect in the annulus fibrosus; and curing said material in situ. This method may include one or more of the following embodiments: curable material is in flowable liquid form; curable material comprising a combination of at least two components, and wherein at least one of said components is a cross linkable material and at least one other of said components is a cross linking agent for said cross linkable material; a cross linking agent that is a polymeric compound having at least two epoxy groups therein; a cross linking agent that is a chemical cross linking agent that is reactive with said cross linkable material; a defect that is an opening in said annulus fibrosus that has been caused surgically; a defect that is an opening in said annulus fibrosus that has been caused by herniation, trauma, natural degeneration, or by dehydration or loss of disc height due to dehydration; the curable material comprises at least one polymeric component; the curable material is cured in situ by the action of heat thereon; the curable material is cured in situ by the action of electromagnetic radiation thereon; the curable material is cured in situ by the action of UV light; the cross linkable material comprises a flowable, semi-solid material; the in situ cured material comprises a visco-elastic bio-compatible material that has physical properties that are at least substantially similar to the physical properties of said annulus fibrosus; the in situ curable material comprises a biological material; the in situ cured material is biodegradable over a period of time that is substantially equal to the period of time during which additional annulus fibrosus material grows to an extent sufficient to fill said defect; the in situ curing is accomplished in less than 2 hours; the in situ curing is accomplished in up to about 40 minutes; the in situ curing is accomplished after at least about 2 minutes; the in situ curing is accomplished after at least about 30 seconds; the cured material comprises a hydrogel; the defect in said annulus fibrosus comprises at least one fissure in the annulus fibrosus; the fissure has been caused by disc degeneration; the injection of the situ curable, bio-compatible polymerizable or polymeric material composition is performed using an apparatus for percutaneous delivery of a sealant comprising: at least two fluid reservoirs, the introducer needle having a distal tip that is in fluid communication with at least one reservoir, a fluid delivery tube that is in fluid communication with a second reservoir, wherein the fluid delivery tube has a tip; the fluid delivery tube is configured so that the tip of the fluid delivery tube does not extend past the distal tip of the introducer needle during use; a pharmaceutically active agent is employed that is selected from the group consisting of growth factors, differentiation factors, enzymes, receptor agonists or antagonists, antibodies, hormones, analgesics, local anesthetics, anti-inflammatory drugs, such as Indomethacin and tiaprofenic acid, TNF-A inhibitors, antibiotics, anti-microbial agents; antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics including local anesthetics such as lidocaine and bupivicaine; analgesics; oncology agents; cardiovascular drugs; nutritional supplements; hormones; glycoproteins; fibronectin; peptides; interferons; cartilage inducing factors; protease inhibitors; vasoconstrictors, vasodilators, demineralized bone or bone morphogenetic proteins; hormones; lipids; carbohydrates; proteoglycans, versican, decorin, and biglycan; antiangiogenins; antigens; DBM; hyaluronic acid and salts and derivatives thereof; polysaccharides; cellulose compounds; antibodies; gene therapy reagents; genetically altered cells, stem cells; cell growth factors; type I and II collagen; collagen hydrolysate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage including autologous cartilage; oxygen-containing components; enzymes such as, for example, peroxidase, which mediate the release of oxygen from such components; melatonin; vitamins; nutrients, and combinations thereof; the injection of the situ curable, bio-compatible polymerizable or polymeric material composition is performed using an apparatus for delivering a biocompatible sealant, comprising: at least two reservoirs for fluids to be delivered, an actuation assembly that causes the fluids to flow out of the reservoir through an exit port in the reservoir, and a pressure monitor coupled to the delivery device to measure pressure within the device; the injection of the in situ curable, bio-compatible polymerizable or polymeric material composition is performed using an apparatus comprises: a multi-barrel syringe, an introducer needle, a fluid delivery tube adapted to receive fluid from a first barrel of the multi-barrel syringe and adapted to extend into the introducer needle, and a connector coupled to a barrel of the multi-barrel syringe, wherein the connector is coupled to the introducer needle and adapted to receive the fluid delivery tube so that the fluid delivery tube extends into the introducer needle, and other embodiments disclosed herein.

In another broad respect, this invention is a kit comprising an in situ curable composition, an introducer needle, and a delivery device for injecting the composition.

In another broad respect, this invention is a method of preparing a kit, comprising providing an in situ curable composition, an introducer needle, and a delivery device for injecting the composition.

The kit and method of making a kit can include the embodiments discussed above with respect to the method of treating a disc as well as other embodiments disclosed herein.

In another broad respect, this invention is a process of injecting the curable composition into the disc such that the curable composition flows outward to repair a ruptured annulus fibrosus, where the nucleus pulposus contains a sufficient number of viable cells, or such cells are co-injected, that assist in the restoration of the load-bearing and viscoelastic properties of the defective intervertebral disc.

In another broad respect, this invention is an implant that minimizes removal of nucleus pulposus material during a discectomy intervention without having an elevated risk of recurrent disc hernia, where the implant has been formed by injecting the curable composition into the disc. Since the nucleus pulposus tissue in most disc hernia patients is viable and has regenerative potential, leaving as much nucleus pulposus tissue as possible in the disc space may be conducive to the gradually regeneration of the disc and restoration of its physiological functions.

The damage to the annulus that is at least partially repaired in accordance with this invention may have, for example, the shape of a complex radial cleft that extends from the innermost edge of the annulus fibrosus, that is at the border of the nucleus pulposus, to the outermost layers of the annulus fibrosus. The defect may be in the form of fissures. These fissures may be the result of traumatic injury to the disc, such as that caused by repetitive or severe twisting when improperly lifting, or severe (axial or lateral) compressive impact to the structures of the spine. Alternatively, the damage to the annulus may have been created by an incision, scrape, or the like. Another type of defect of the annulus fibrosus is often observed in the case of severely degenerated intervertebral discs. In this condition, the disc tissue has become severely dehydrated and has lost its elasticity. As a result, the annulus fibrosus tissue has become brittle, friable and unstable to the extent that tissue fragments may come loose and migrate out of the annulus fibrosus, leaving space through which nucleus pulposus material can exude. These fragments are separated from the main body of the annulus fibrosus by numerous interconnecting fissures and are often held in place only by a thin outer lamella of the annulus fibrosus. When this thin layer tears, the fragments may migrate into the epidural space and cause pressure on the spinal nerves, that in turn may cause severe pain. Thus, the defect repaired during the practice of this invention can be a tear of the annulus fibrosus, a fissure in the annulus fibrosus, and the like. This treatment serves to reduce the amount of material from the nucleus fibrosus that leaks through the defect(s) in the annulus fibrosus. Advantageously, injection of the curable composition sealant can also serve to restore normal disc height and physiologic hydrostatic pressure, key components to disc health. It should be understood that normal physiologic hydrostatic pressure can vary from person to person, and that the treatment may produce near-normal hydrostatic pressure. As used herein, normal physiologic pressure encompasses this range of pressures. In one embodiment, neither the nucleus pulposus nor the annulus fibrosus has been heated in the body to stiffen the disc either prior to or concurrent with the injection, such as discussed in for example U.S. Pat. No. 6,095,149. In one embodiment, in the practice of this invention the nucleus pulposus has not been removed by surgery, such as in the case of a total or partial discectomy or by nucleoplasty for a herniated disc. The defects to be at least partially repaired in accordance with this invention can be caused by a variety of occurrences such as but not limited to being caused by trauma, by natural degeneration, and by dehydration or loss of disc height due to dehydration.

Advantageously, the method and kit of this invention facilitate extended pain relief for patients with leaky disc syndrome, wherein for example nucleus pulposus leaks out of the disc through defects (e.g. tears or fissures) in the annulus fibrosus. The pressure monitor provides a heightened level of safety whereby the physician can measure pressure in real time so as to avoid over-pressurizing a disc being treated. Likewise, the physician can observe the pressure reading in conjunction with injection of the fibrin sealant to determine whether the disc is being sealed and whether sufficient fibrin sealant has been injected. In this way the physician can use the delivery device as a diagnostic tool to assess whether the disc is treatable.

Injecting of curable composition as used herein thus encompasses any injection of components in the disc, including circumstances where a portion of the components being curing due to mixing prior to contact with or actual introduction into the disc. In one embodiment, the mixing of the components at least partially occurs in, for example, a Y-connector or within the introducer needle. Alternatively, mixing and cure occurs after the components are pushed out of the fluid delivery device and introducer needle, such as when the fluid delivery tube extends out past the introducer needle.

It should also be appreciated that the point, or points, of injection (e.g., at the tip of a spinal needle) can be within the annulus fibrosus or in the nucleus pulposus. If the injection occurs in the nucleus pulposus, the injected components may form a patch at the interface between the nucleus pulposus and the annulus fibrosus, or, more commonly, the components flow into the defect(s) (e.g., fissures) of the annulus fibrosus and potentially "overflowing" into the interdiscal space. In practice, over-pressurizing the disc by injecting the components into the disc should be avoided.

A contrast agent may be used in conjunction with the injection of the curable composition. The contrast agent may be injected prior to injection of the curable composition. Alternatively, the contrast agent is included in the curable composition that is injected. Contrast agents and their use are well known to one of skill in the art.

In general, the curable composition of this invention is injected into the disc, the epidural space, the zygapophyseal joints (aka: facet joints), and/or sacroiliac joint. With respect to an injection of curable composition into a disc, an intradiscal injection serves to create a cured composition which seals the disc from leaking material from the nucleus into the area outside the disc. For example, the curable composition can be delivered by fluoroscopic transforminal lumber epidural or intra-discal injection, such as described in U.S. Pat. No. 6,468,527. For the treatment of back injuries such as these, the curable composition is injected into the nucleus pulposus, to fill any fissures or voids of the annulus fibrosus, to seal the bone end plates to the disc, increase pressure of the disc, and to increase the height of the disc space. In general, the curable composition is injected at a location near the defect in the annulus fibrosus. Typically the curable composition will flow into the fissures in the annulus fibrosus, and some may thus flow out of the intra-discal space. The injection may also serve to coat areas adjacent to the disc, directly on the nerve roots and surrounding areas which serve to protect those areas from the effects of the leaking nucleus material. Sealing the fissures and bone end plates halts the leakage of harmful chemicals from the disc environment and prevents the initiation of foreign-body reactions towards the damaged disc and nociceptors in the outer annulus of the disc by the immune system. Increasing the disc space relieves pressure on the nerve root. That is, as a result of the injection, an increase of the disc height occurs, which increases the spacing between lamina, and which in turn relieves pressure on the nerve roots on the lamina. For this application, supplementation of the curable composition with growth factors and a variety of biologically or pharmaceutically active agents, including tumor necrosis factor inhibitors (TNF-α inhibitors) may promote rehabilitation of the damaged tissues or the gradual replacement of the curable composition with healthy tissue and/or reduce inflammation in surrounding tissues.

BRIEF DESCRIPTION OF THE DRAWINGS

FIG. 4 shows a semi-exploded view of one embodiment of the device of this invention.

FIGS. 9-11 show one embodiment of the needle assembly of this invention.

FIGS. 19A-19C show additional embodiments of the apparatus of this invention.

FIG. 20 shows an additional embodiment of the apparatus of this invention during use.

DETAILED DESCRIPTION OF THE INVENTION

Figure 1A:
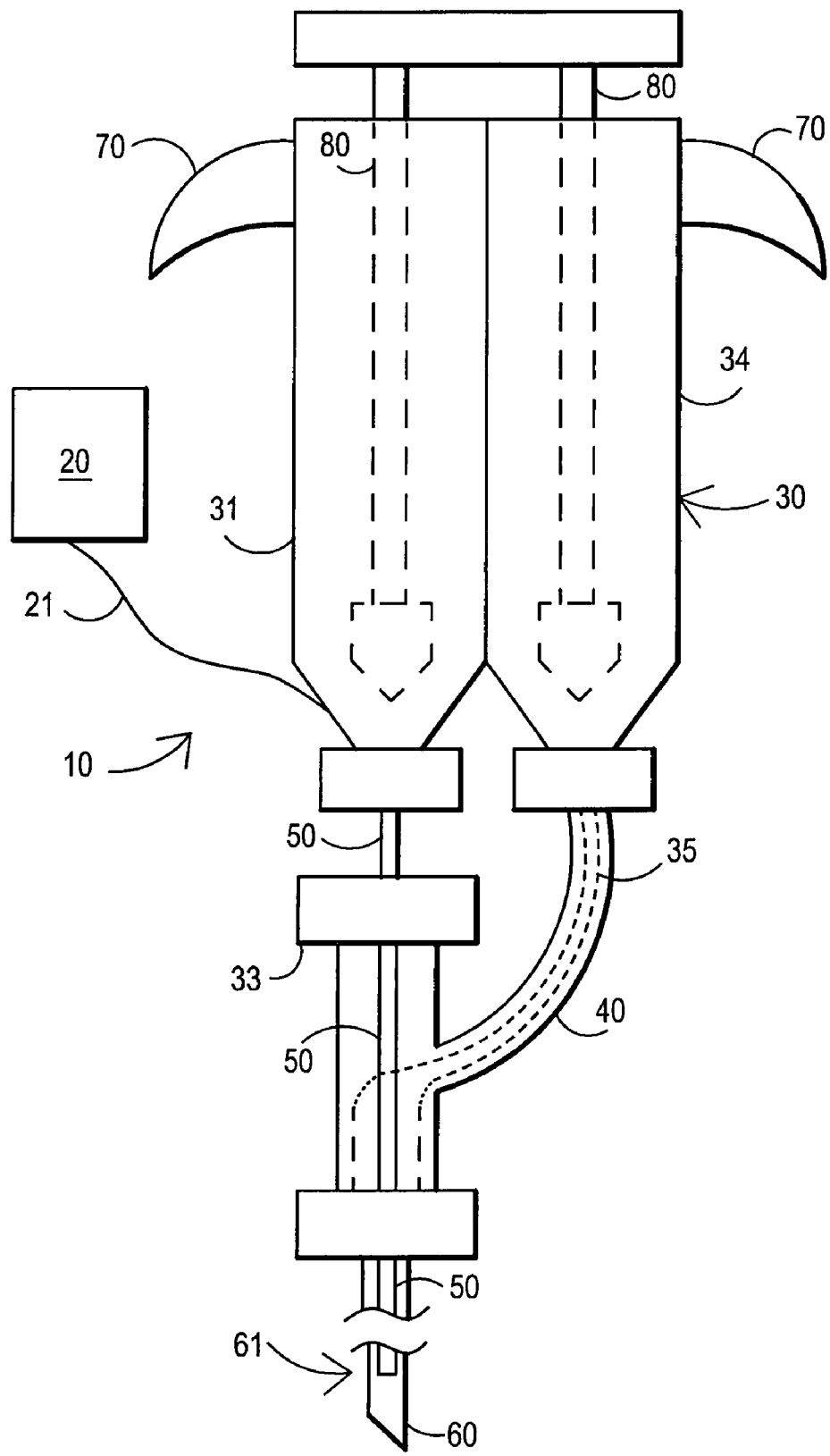
FIGS. 1A, 1B and 1C show representative delivery devices of this invention.

In the practice of the present invention, for repairing defects of the annulus fibrosus, the sealant composition of this invention is applied by injecting the material into the disc. Thus, the curable composition is in a form that is injectable. Rather than injecting the composition into the proximity to the defect as per U.S. Pat. No. 6,428,576, the material is injected according to this invention by introducing an introducer needle into the disc by inserting an introducer needle through the annulus (puncturing the annulus) and into the nucleus pulposus, inserting a fluid delivery tube into the introducer needle, and injecting the curable composition through the fluid delivery tube (optionally also through the introducer needle) to thereby in a more superior fashion fill and close incisions, clefts or fissures in the annulus fibrosus, and so on, such as occur after a disc hernia has been surgically treated. The curable composition can be injected, for example, using the procedure and delivery device for injecting fibrin sealant described in U.S. Pat. No. 6,468,527, incorporated in its entirety herein by reference. Of course, other delivery devices can also be employed so long as the device is capable of injecting the curable composition into the disc so that the curable composition moves outwardly toward the exterior of the disc to thereby at least partially repair the annulus after in situ cure of the composition.

The intervertebral disc is sealed in order to prevent a later extrusion of further disc material. This procedure is useful where the remaining nucleus pulposus is comprised of a sufficient amount of viable cells to perform its function. That is, this procedure is most useful where the amount of nucleus pulposus remaining in the disc after effecting repair is sufficient for the disc to continue to perform its intended function.

In addition, in the practice of this invention, rather than using the curable composition to patch up or consolidate brittle and friable tissue that exists in the outer annulus fibrosus of a severely degenerated intervertebral disc by providing the composition in the vicinity of the damaged tissue, the curable composition is injected directly into the disc. Thus, rather than serving as a putty or cement in order to bind together the remaining tissue fragments of the outer annulus fibrosus, the composition flows from inside the disc toward the periphery of the annulus and cures in situ within annulus to thereby at least partially repair the annulus. This application of the practice of this invention could also be described as annulus augmentation or partial annuloplasty, where the brittle annulus fibrosus is reinforced and stabilized through the in-situ curing of a sealant according to this invention. This application of the invention is intended to prevent tissue fragment migration and thus reduces the risk of spinal nerve compression by sequestrated fragments of the degenerated annulus fibrosus.

The bio-compatible compositions, comprising the in situ curable sealant of this invention, are based on materials that range in viscosity and physical state from an injectable liquid to a visco-elastic solid. The materials are preferably prepared from human or animal origin or may be made through conventional chemical synthesis or by a recombinant DNA technique. In general, it is important that the bio-compatible material compositions have the property of forming, upon curing, a strongly bonding, visco-elastic material that becomes sealed to the annulus fibrosus, or to fragments thereof, within about 2 to 40 minutes, preferably 2 to 10 minutes, after application (by injection or otherwise). The in-situ curing process must work well under wet conditions, at or near physiological pH (e.g. a pH of about 5-10), at or near physiological temperature (e.g. about 4-50, C) and in the presence of interstitial body fluids (such as spinal fluid and/or blood). The sealant must cure to create a non-toxic, bio-compatible and strongly tissue adhesive seal of the annulus fibrosus or of materials that make up this feature. It should be of sufficient strength to stay in place without decomposition under permanent cyclic physiological loads.

A bio-compatible material that can serve as sealant of the annulus fibrosus preferably meets characteristics with regard to its strength, tissue adhesion properties and bio-compatibility both when injected and after curing.

Various bio-compatible material compositions have been described in the art. Some of these may be useful as in-situ curable sealants for defects of, or incisions in, the annulus fibrosus. None of the published disclosures of biomaterial compositions describe the potential application of such materials as in-situ curable sealants for use in connection with repair of the annulus fibrosus. Furthermore, none of the applications for the various bio-compatible materials that have been described in the prior art are similar or comparable to the use of such a sealant in connection with damaged annulus fibrosus. There are no disclosures in the prior art that described applications in which an uncured liquid bio-compatible material is caused to be injected into a joint or disc to flow outward toward the periphery of the joint/disc to at least partially fill voids and seal defects, and therein to become cured whereby to seal or patch up the defect. There is no disclosure in the prior art that shows using such sealants bio-compatible materials to prevent re-herniation of the annulus fibrosus, or prevent, or at least minimize, annulus fibrosus tissue migration. Thus, this invention provides an annulus fibrosus sealing means, formed from in-situ curable formulations comprising injectable bio-compatible material, that can be caused to cure in situ.

Preferred bio-compatible materials for use in the practice of the invention include all bio-compatible, hydrophilic synthetic or naturally occurring polymers that are curable to a visco-elastic end product under physiologic conditions. These polymers are cross-linked by an internal mechanism. That is, in some cases, no outside energy input or material is needed to cause the flowable bio-compatible polymers of this invention to become cured into a relatively permanently placed visco-elastic material. In other situations, the flowable bio-compatible polymers of this invention will need the input of outside influences, such as irradiation and/or heat, to cause them to cross link and become the desired visco-elastic materials. Such heat and/or irradiation can be very localized so as to cause the cross linking and curing to occur exactly where it is needed. In either case, the end product cross linked visco-elastic polymer materials will maintain its location, shape and structure, and lend stability and physical strength to a damaged annulus fibrosus. This can be on a permanent basis, that is the repairing sealant will become a permanent part of the annulus fibrosus.

It is also within the scope of this invention that the visco-elastic sealant used in this invention will be a temporary material that will bind and repair the damaged annulus fibrosus for a time sufficient to prevent re-injury of this member and to enable scar formation with fibrocartilaginous tissue to occur. This type of sealant will be composited such that it will degrade with time so that by the time the annulus fibrosus has accomplished sufficient self repair, the added sealant will have degraded and be expelled from the body. This cross-linking can be accomplished by making up a flowable mixture of two or more precursors molecules that react with each other over a short time to form the desired in situ cured visco elastic product that has physical and chemical properties that resemble those of the annulus fibrosus sufficiently to perform its function, at least substantially, while the natural annulus fibrosus regenerates itself. This flowable, in situ curable material may be made up of a single precursor that reacts with itself, e.g. by heating, or by irradiation with electromagnetic energy, such as visible or ultra violet light. It is also within the scope of this invention to use a one or plural component curable flowing material that is cured by the action of a catalyst and/or initiator that is included in the composition.

Some or all of the chemical compounds, cross linkable polymers, or pre-polymers, that form the precursor materials, or are the building blocks from which the precursor components are formed, can be bio-compatible, hydrophilic synthetic or naturally occurring polymers. Even if some of the precursor components are not especially bio-compatible, since they are intended for use within an animal, especially human, body, it is essential that none of these precursor materials themselves nor the polymers that result from their curing be detrimental to the animal, especially human, host. The cured polymer products are preferably completely bio-compatible, e.g. they do not induce extensive chronic inflammation, do not induce excessive complement activation, and do not induce excessive local cytotoxicity, such as for example as a result of components that leach out of these cured or uncured materials. It is important that the cured polymers be hydrophilic, so as to form materials that are hydrogels, e.g. polymers with absorbed water contents in excess of approximately 25% of their own weight. The tissue specific compatibility of the resulting hydrogels is generally better than is the case with less hydrophilic materials. This is as a result of the water permeability of the hydrogel being similar to that of the surrounding tissue, and because of the better matching of the mechanical properties of the instant sealing material with the surrounding natural annulus fibrosus tissue.

The cured polymers that are useful in this invention may be synthetic or naturally occurring. It may be more reliable to ensure the long-term stability of a cured sealant that is based on synthetic polymers.

Alternatively, a controlled degradation can be engineered into a synthetic polymer by incorporation of slowly hydrolyzable linkages, such as for example ester, amide, carbonate or anhydride linkages, into the cured polymer. Naturally occurring polymers generally will form sealing members that become more easily degraded in vivo, and there may be cases in which this is desirable, e.g. when the sealant is intended to be replaced by natural tissue that is being generated as a result of healing in the annulus fibrosus. This may be particularly desirable when the cured sealant member contains a bio-active agent to promote healing.

Examples of the type of synthetic polymers that can be used as building blocks in accord with this invention are polyethylene glycol, polyvinyl pyrrolidone, polyvinyl alcohol, polyacrylic acid, polyethoxazoline, polyhydroxyethyl acrylate, and polyhydroxyethyl methacrylate. These materials can be further functionalized in order to increase their ability to form hydrogels gels in situ.

Polysaccharides that are useful in the present invention include glycosaminoglycans such as hyaluronic acid, chondroitin sulfate A, chondroitin sulfate C, dermatan sulfate, keratan sulfate, chitin, chitosan, heparin, and derivatives or mixtures thereof. Further, proteoglycans such as decorin, biglycan and fibromodulin may also be used in the present invention. Proteoglycans are components of the extracellular matrix of cartilage cells and contain one or more glycosaminoglycan molecules bound to a core protein. Furthermore, mixtures of various species of glycosaminoglycans or proteoglycans with various proteins, or mixtures of various species of glycosaminoglycans or proteoglycans with proteins can be used in the practice of the present invention.

Various synthetic polypeptides can also be used in the practice of the present invention. The term "synthetic polypeptide" is intended to encompass polypeptides that have been produced using recombinant DNA techniques, as well as those produced by other methods of chemical synthesis.

Various naturally occurring proteins such as albumin, collagen, fibrin and elastin may also be used alone or in combination with other materials in the practice of the present invention.

The terms "albumin" "collagen" or "elastin" or "fibrin" as used herein refer to any types of these naturally occurring proteins, from any source, including, but not limited to, protein extracted from tissue or fractionated from blood or recombinant proteins. Further, these terms refer to all forms of these naturally occurring proteins, including those that have been processed, denatured or otherwise modified.

In general, collagen, elastin, fibrinogen or fibrin from any source may be used in the practice of the present invention. The preparation of purified, non-immunogenic proteins from human or animal tissues as well as recovered by different methods of producing recombinant human collagen or fibrin are thoroughly described in the literature.

Collagen of any type, including, but not limited to, types II, III, V, VI, IX or any combination thereof, are preferred to be used in the practice of the present invention, although collagens of type I and type II are generally the most preferred types. Collagen for use in the present invention may be in a fibrillar or non-fibrillar form. The preferred form of the preferred collagen for the practice of the present invention is the fibrillar form of collagen due to its higher persistence and mechanical strength.

Elastin of any type can be used for the practice of the present invention. Elastin of type I is generally preferred.

In a preferred embodiment of the present invention, the sealant for the damaged annulus fibrosus is a bio-compatible polymer composition of viscosity that is sufficiently low to permit injection and which forms a visco-elastic material upon becoming cured. The bio-compatible polymer precursor(s), when implanted in the situs of the defect in the annulus fibrosus, are flowable material(s), preferably a liquid of suitable viscosity such that when the liquid conforms to the damaged area of the annulus fibrosus, it tends to stay in place while it is curing in situ.

In general, the preferred material composition for use in the practice of the invention is an in-situ curing, bio-compatible polymer composition that has, when cured, the properties of an elastic, or visco elastic, substantially solid hydrogel. The preferred bio-compatible polymer material composition may include two or more precursor components that are dissolved or dispersed in two different solvents/carriers, A) and B). The solutions/suspensions are suitably mixed immediately prior to the injection of the sealant. Alternatively, a single solution containing the appropriate bio-compatible material composition can be used in combination with a separate initiator system to start the curing reaction, as for example the composition disclosed for a different purpose in U.S. Pat. No. 5,626,863.

A preferred bio-compatible material composition that is useful for sealing damage to the annulus fibrosus is made of two precursor components, a bio-compatible material solution and an activated crosslinking agent. In this preferred composition, bio-compatible materials, such as collagen or glycosaminoglycans, and cross linking agents, such as synthetic hydrophilic polymers as disclosed for a different purpose in U.S. Pat. No. 5,324,775 or 5,328,955, can be used. Preferred synthetic hydrophilic polymers for use in the invention include bifunctionally activated polyethylene glycols, as disclosed for a different purpose in U.S. Pat. No. 5,328,955 or 5,583,114.

Another preferred bio-compatible material composition for the sealant of a damaged annulus fibrosus is made of two precursor components, a buffered protein solution and a bifunctional cross linking agent. More specifically, the protein is preferably a non-immunogenic, water soluble protein. Materials such as serum albumin or derivatives of elastin, fibrinogen or collagen can be used as protein, and polyethylene glycol, with activated terminal groups may be used as the preferred cross linking agent in this preferred composition. Such a composition is disclosed for other purposes in U.S. Pat. No. 5,583,114.

Another preferred bio-compatible material composition that is useful for the sealant of the annulus fibrosus according to this invention is made of a polymerizable component that includes a water soluble core region and polymerizable terminal group(s) or functional group(s). In addition, the component may include a biodegradable extension of the core region. A preferred embodiment of this aspect of this invention includes polyethylene glycol as the core region and one or more acrylate moieties as the polymerizable end cap or terminal portion, as disclosed for other purposes in U.S. Pat. No. 5,626,863. In the practice of using this component as in-situ curable sealant for the damaged annulus fibrosus, a free radical polymerization reaction of the component must be initiated, either after the composition has been placed at the situs, or immediately prior to introduction of the composition into the damaged area(s) of the annulus fibrosus. For initiation of the polymerization immediately prior to application, the polymerizable component may be extruded from a syringe or a piston-driven cartridge and passed through a light or temperature conducting cannula before it reaches the situs of the annulus fibrosus defect. The free radical polymerization reaction may be initiated through photo-initiation by UV or visible light irradiation of the cannula. In the case of a thermal polymerization initiator system, as disclosed in U.S. Pat. No. 5,826,803, the cannula may be heated to a controlled temperature that is not higher than about 48 degrees C. For initiation of the free radical polymerization reaction in situ, either a thermal polymerization initiator system, that is sensitive to a temperature of about 37 degrees C. or, alternatively, chemical initiation systems may be used in the practice of the present, invention. Such systems are disclosed for other purposes in U.S. Pat. No. 5,626,863.

A particularly preferred bio-compatible material composition that is useful for sealing damage in an annulus fibrosus is made of two precursor components that can co-polymerize in a self-selective manner, such as by a nucleophilic addition reaction, as disclosed in U.S. Pat. No. 6,958,212, incorporated in its entirety herein by reference. In a preferred embodiment, a hydrophilic linear or crosslinked polymer with two or more terminal unsaturated groups is used as the first precursor component, and another hydrophilic polymer with two or more terminal nucleophilic groups is used as the second precursor component. In a particularly preferred embodiment, polyethylene glycol constitutes the hydrophilic polymer, acryloyl moieties are used as unsaturated end groups, and compounds with thiol functional groups are used as the nucleophilic groups. Such compositions are disclosed in this provisional patent application.

When using this embodiment in the practice of the present invention, the two precursor components should be quickly mixed immediately prior to use and then applied to the annulus fibrosus defect using a common applicator. As a preferred embodiment, the two components may be filled into a dual syringe or a dual-chamber piston-driven cartridge. Both chambers of the syringe, or the cartridge, have openings that merge together into one outlet tube. This tube, is fitted with a suitable mixing nozzle, such as a spiral mixer nozzle, that serves as a static mixer for the two components when they are pressed out of the syringe and passed through the nozzle. As the mixed components are pressed out of the tip of the nozzle, they can be injected into the joint/disc.

It is desirable for the mixed bio-compatible material composition to have a low surface tension in relation to physiological materials such as fluids and the annulus fibrosus, and a good intrudability into such systems. These properties permit the bio-compatible material to optimally penetrate into micro-fissures that may be present at the application site of the annulus fibrosus. The intrusion of the biomaterial into micro-fissures and clefts of the damaged annulus fibrosus allows for a strong mechanical interlocking with the natural tissue at the application site and helps to mechanically secure the sealant within the application site during the curing time.

The term "intrudability" relates to the ability of a liquid material composition to penetrate into complex microstructures and to fill small voids. This intrusion or penetration into said microstructure may be caused by low injection pressures, gravitation, capillary forces or non-covalent interactions between the liquid and the microstructure. The intrudability of the mixed biomaterial composition can be increased by including one or more bio-compatible fluid lubricants or surfactants, for example dextrose, maltose, glycogen, dextran, dextran sulphate, hyaluronic acid glycerol, phospholipids polyoxyethylene sorbitan esters or polyethylene/polypropylene glycols.

Various particulate materials may also be incorporated into the bio-compatible material compositions for use in the invention. Suitable particulate materials include, without limitation; particulate elastin fibers and crosslinked or non-crosslinked fibrillar collagen.

Various biologically or pharmaceutically active agents may also be incorporated into the bio-compatible material compositions for use in the invention. Examples of active agents include, without limitation, growth factors, differentiation factors, enzymes, receptor agonists or antagonists, antibodies, hormones, analgesics, local anesthetics, anti-inflammatory drugs, such as Indomethacin and tiaprofenic acid, antibiotics or anti-microbial agents. Additional additives may be employed in the fibrin sealant such as, but not limited to: antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics including local anesthetics such as lidocaine and bupivicaine; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans such as aggrecan (chondrotin sulfate and deratin sulfate), versican, decorin, and biglycan; antiangiogenins; antigens; DBM; hyaluronic acid and salts and derivatives thereof; polysaccharides; cellulose compounds such as methyl cellulose, carboxymethyl cellulose, and hydroxy-propylmethyl cellulose and derivatives thereof; antibodies; gene therapy reagents; genetically altered cells, stem cells including mesenchymal stem cells with transforming growth factor, and/or other cells; cell growth factors to promote rehabilitation of damaged tissue and/or growth of new, healthy tissue such as BMP7 and BMP2; type I and II collagen; collagen hydrolysate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage including autologous cartilage; oxygen-containing components; enzymes such as, for example, peroxidase, which mediate the release of oxygen from such components; melatonin; vitamins; and nutrients such as, for example, glucose or other sugars, and combinations thereof. However, it is foreseeable that any of these additives may be added to the fibrin sealant separately or in combination. The term "active agent" as used herein refers to molecules, usually organic, that exert biological effects in vivo. This term also encompasses combinations or mixtures of two or more active agents.

The patents listed above describe various methods of using in-situ curable bio-compatible material compositions in the field of soft and hard tissue surgery, such as to position tissue flaps, to attach side grafts, to prevent air leaks in pulmonary surgery, to inhibit bleeding, to avoid unwanted tissue adhesions, to fill and augment any void spaces in the body, or more generally to close undesired lesions and fissures such as fistular orifices or cysts.

However, these prior art patents do not describe or mention an application or method of using such materials as an in-situ curing sealant to treat defects in the annulus fibrosus and thereby to create an annulus sealing device. There is also no prior art that describes applications that are similar or comparable to the specifications and objectives of a sealant for the annulus fibrosus, as described in the following two sections. Specifically, none of the prior art describes applications in which a liquid or semi-solid biomaterial is caused to flow into a complex three dimensional annulus fibrosus tissue defect, to seal or patch up the defect and prevent a re-herniation or annulus tissue migration, and assists to restore, at least partially, the hydrodynamic function of the intervertebral disc.

Thus, there is described an annulus sealing device, comprising in-situ curable biomaterial formulations that cure to a visco elastic member that at least partially simulates the structure, physical properties and biomechanical functions of the annulus fibrosus and maintains the integrity of this member permanently or for a time sufficient to enable the regeneration of the natural annulus fibrosus tissue.

Because of the unique bio-mechanical and physiological properties of the intervertebral disc in general and the annulus fibrosus in particular, a functioning and efficient sealant for the annulus fibrosus should meet numerous specifications, even if it replaces just a small portion of the damaged natural tissue of the annulus fibrosus.

The sealant of the annulus fibrosus is implanted in a low-viscosity liquid form, thus allowing the implanting material to penetrate into tears and micro-fissures with a width of at least 50 micrometers (approximately=the width of a human hair) that are interconnected with a radial rupture or principal defect of the annulus fibrosus.

The sealant of this invention for the annulus fibrosus has the property of becoming strongly attached to the surrounding tissue of the annulus fibrosus by close interlocking and entanglement of its shape with the structure of the annulus fibrosus surrounding the defect and by filling cavities in the nucleus that were created during discectomy, thus forming an inner portion of the implant that has a larger cross section than the protrusion canal. The adhesion of the sealant to the surrounding annulus fibrosus tissue is enhanced through polar group interaction or chain inter penetration between the hydrophilic implant material and the surrounding tissue. In addition, covalent bonds formed between the preferred hydrogel bio-compatible material and the surrounding annulus fibrosus tissue further increase and secure the attachment of the sealant of this invention to the annulus fibrosus tissue in proximity to the defect in the annulus fibrosus.

The annulus sealing material that seals the defects in the annulus fibrosus may be the result of the interaction of at least two bio-material precursor components that react with each other in situ, preferably in a self selective reaction. Alternatively, a single bio-compatible material precursor composition that is activated for polymerization, such as for Example by activation either in situ or application immediately prior to implanting, may be used. Both systems result in a sealant that substantially perfectly conforms to the complex and irregular shape of an annulus fibrosus defect and bonds strongly to the tissue surrounding the defect. In addition, the self-selectivity of the reaction is an important feature to minimize toxic or denaturing effects of the curing bio-compatible material composition.

The sealant of the annulus fibrosus is preferably formed from previously pre-polymerized materials that are employed as prepolymer or macromer precursor components. In this way, the risk of exposing a patient to volatile and toxic residual monomers that may remain after curing of the sealant can be avoided.

The sealant of the annulus fibrosus must have adequate impact and tensile strength and must be adequately resistant to fatigue from repetitive loading and unloading or repetitive torsion moments that the annulus fibrosus is conventionally subjected to. This allows the sealant to permanently stay in place and remain intact after implantation. An even more important property of the sealant of the annulus fibrosus is its ability to withstand intradiscal pressures of the nucleus pulposus in the upper physiological range and to efficiently seal the annulus fibrosus so that the nucleus pulposus is contained within the intervertebral disc.

The sealant of the annulus fibrosus closes the defect in the annulus fibrosus so as to reduce the risk of a recurrent disc hernia and to prevent the further extrusion of nucleus pulposus material through the defect, thus avoiding contact between nucleus pulposus cells and its cytokines or mediators with nerve roots and/or nociceptors found in the outer ⅓ of the disc annulus after discectomy and preventing or minimizing nucleus pulposus-induced nerve root injury and nerve root pain.

The sealant of the annulus fibrosus assists in the restoration of the physiological function of the herniated intervertebral disc. In particular, the sealant of the annulus fibrosus assists the nucleus pulposus to restore its hydrodynamic function after a discectomy intervention by being able to gradually build up the physiological intradiscal pressure. This will also allow the intervertebral disc to act as a cushion for physiological cyclic loads and to gradually restore the normal disc height and thus protect the facet joints in the damaged segment from excessive and long term loads.

The sealant of the annulus fibrosus has adequate viscoelastic properties due to its water content and strong three dimensional network of interconnecting polymer molecules. This minimizes the creep behavior of the sealant and enables it to withstand cyclic loads under physiological conditions for long periods without significant degradation and without losing elasticity.

The material composition for the sealant of the annulus fibrosus may be radio-opaque to a similar degree as a polymethyl-methacrylate based bone cement that is commonly used for the fixation of joint replacement prostheses. This feature is intended to allow the surgeon to monitor the correct implantation of the implanted sealant per-operatively and to identify the implant post-operatively in an X-ray radiograph. This may alternately be accomplished with the addition of a radio-opaque contrast media to the material composition.

The preferred final water content of the cured implant is about 30% to 90%. Generally, the final implant water content increases as the concentration of PEG (polyethylene glycol) in the precursor component solutions decreases.

According to this invention, the sealant of the annulus fibrosus is highly bio-compatible and is well tolerated in the body due to its following properties: A) it is preferably a hydrogel material that is hydrophilic and water-permeable similar to the surrounding tissues, B) the sealant material is non-toxic and C) the sealant material has a stiffness coefficient, in relation to the application of physiological loads and stresses, such as in compression, tension, and axial rotation, that is the same as or less than the stiffness coefficient of the natural annulus fibrosus tissue.

By being as strong as, but softer than, the surrounding tissue, friction, if any, between implant and surrounding tissue remains low and stress-shielding of the tissue is avoided. By avoiding friction with the implant and stress-shielding of the surrounding tissue, the conditions for a normal long term remodeling of the annulus tissue are optimized and the risk of gradual implant rejection or hypertrophic tissue reactions is minimized. The sealant for the annulus fibrosus is permeable to water and water soluble substances, such as nutrients, metabolites, drugs and the like.

The sealant for the damaged annulus fibrosus may also serve as a carrier and controlled release drug delivery system for applications of drugs for anti-inflammatory, antibiotic, analgesic or other therapies. In the case of a non-biodegradable sealant for the annulus fibrosus, the release mechanism is primarily based on diffusion of the drug through the cross linked sealant and into contact with other elements of the body where therapy is required. In the case of a hydrolytically stable, bioerodible material composition for the sealant, the drug release rate will be steady and predictable and will be proportional to the controlled bioerosion of the sealant material over an extended period of time, while newly formed annulus fibers and nucleus tissue gradually replace the sealant material put in place according to this invention.

Preferably, the sealant for the annulus fibrosus may also function as a carrier for the controlled release of various growth and/or differentiation factors, such as basic fibroblast growth factor (bFGF), insulin-like growth factor (IGF), transforming growth factor beta (TGF), platelet derived growth factor (PDGF), chondromodulin (ChM), bone morphogenic protein (BMP), etc. For the successful administration of these auto- or paracrine growth factors, a biologically relevant concentration must be maintained in the disc tissue over an extended period of time. It should be noted, for example, that OP-1 (BMP-7) is a very sticky molecule; however, if not held within the confines of the disc annulus and allowed to leak out of the disc, it is completely resorbed by the body within a few minutes. Due to its proximity to the annular lesion, the sealant for the annulus fibrosus, when used as a carrier for the controlled release of growth factors, may allow for an excellent bioavailability of the mentioned growth factors covering a therapeutic window of several weeks or months.

Preferably, the sealant for the annulus fibrosus may also function as a carrier for the controlled release of various cytokine blockers to retard the proinflammatory effects of TNF-α. TNF-α over-expression has been documented in a number of inflammatory processes which led to the first successful attempts to block a cytokine therapeutically. A monoclonal antibody to TNF-α or infliximab, was originally piloted in rheumatoid arthritis and Crohn's disease. In both cases the therapeutic effect was dramatic with dose-dependent clinical and laboratory responses. The original rationale for the use of antibodies to TNF-α in rheumatoid arthritis was the finding that the two predominant cytokines in synovial fluid are IL-1 and TNF-α [1]. These two cytokines act both directly and indirectly. For example, IL-1 and chemokine production are driven largely by the TNF-α. TNF-α acts directly by promoting the release of metalloproteinases and leukotrienes which are responsible for tissue damage.

In the preferred form of the invention, the precursor components are stored in a piston driven, one or two chamber cartridge that serves as a transport and storage container. Each chamber of the cartridge is closed by a sealing membrane within the extrusion flange at the tip of the cartridge.

The sealant for the damaged annulus fibrosus; can be applied sub-cutaneously and/or post operatively at the end of a standard micro-discectomy surgery with the patient in prone position. For application of the sealant, the cannula of the prepared application system is placed deep into the defect or incision of the annulus fibrosus in such a way that the tip of the cannula is proximate to the inside edge (that is the edge of the annulus fibrosus that boarders on the nucleus pulposus) of the cavity created by removal of disc tissue during discectomy. This placement is followed by injecting the precursor components of the sealant of this invention into the defect until the defect is completely filled, which typically requires ½ to up to about 2 ml of precursor component volume. As the precursor components are pressed out of the cartridge, they are mixed in the nozzle and, dependent on the bio-compatible material composition used, the polymerisation or nucleophilic addition reaction, that results in the curing of bio-compatible material composition, is initiated. Because of its low viscosity and low surface tension as compared with physiological fluids, the mixed precursor components are able to penetrate into micro-fissures in the degenerated or remaining (after the discectomy) annulus fibrosus tissue that are interconnected with the radial cleft.

In the preferred form of the invention, the two precursor components of the sealant cure in situ within more than about 30 seconds but less than about 10 minutes to form a semi-solid or solid visco-elastic polymer hydrogel implant that conforms to the shape of the annulus fibrosus defect. The thus formed implant becomes closely interlocked with the annulus fibrosus structure that surrounds the defect and is inherently shaped to conform, when cured, to the shape of the defect in the annulus fibrosus that it has filled.

Figure 1B:
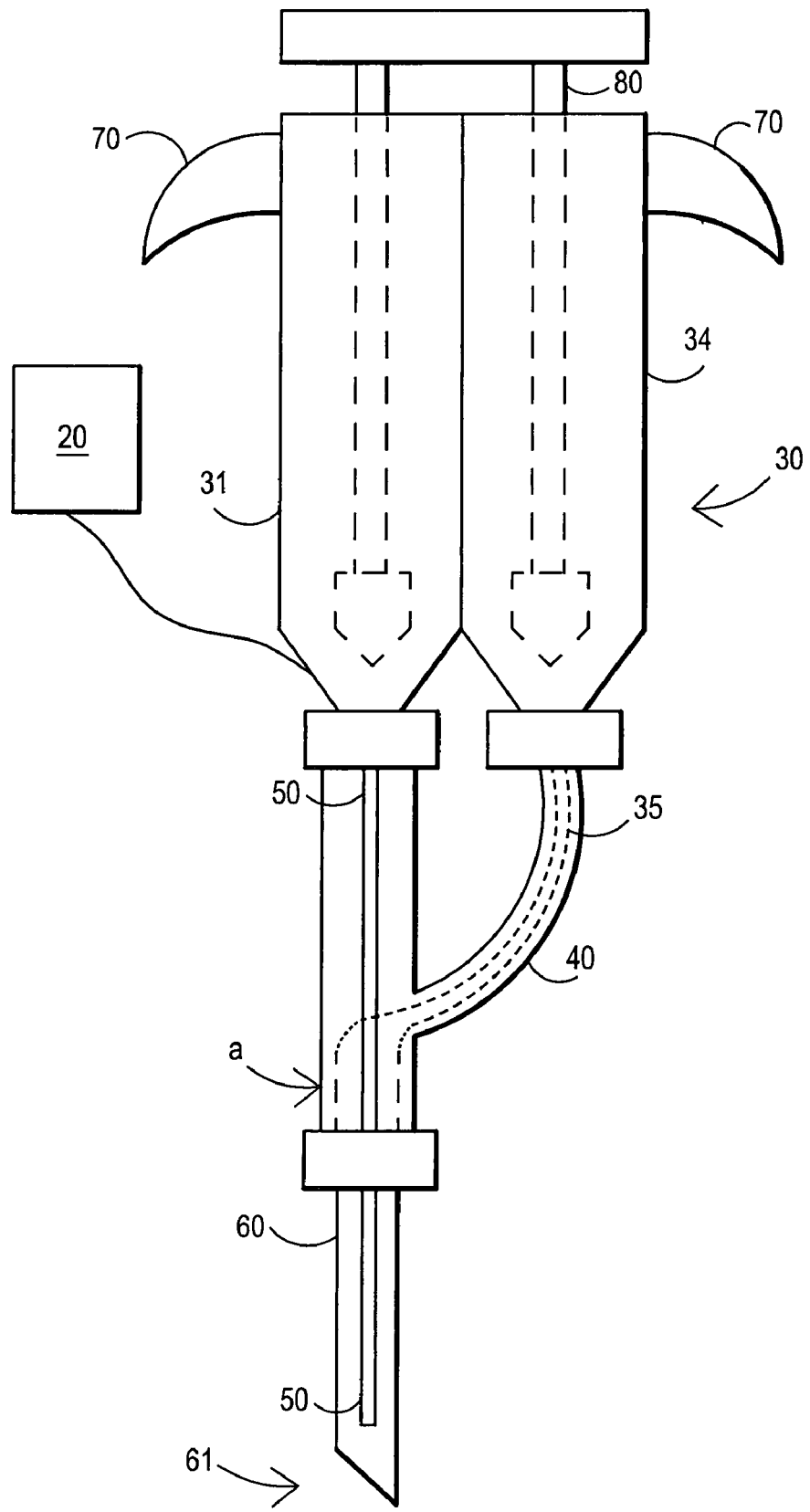
Figure 1C:
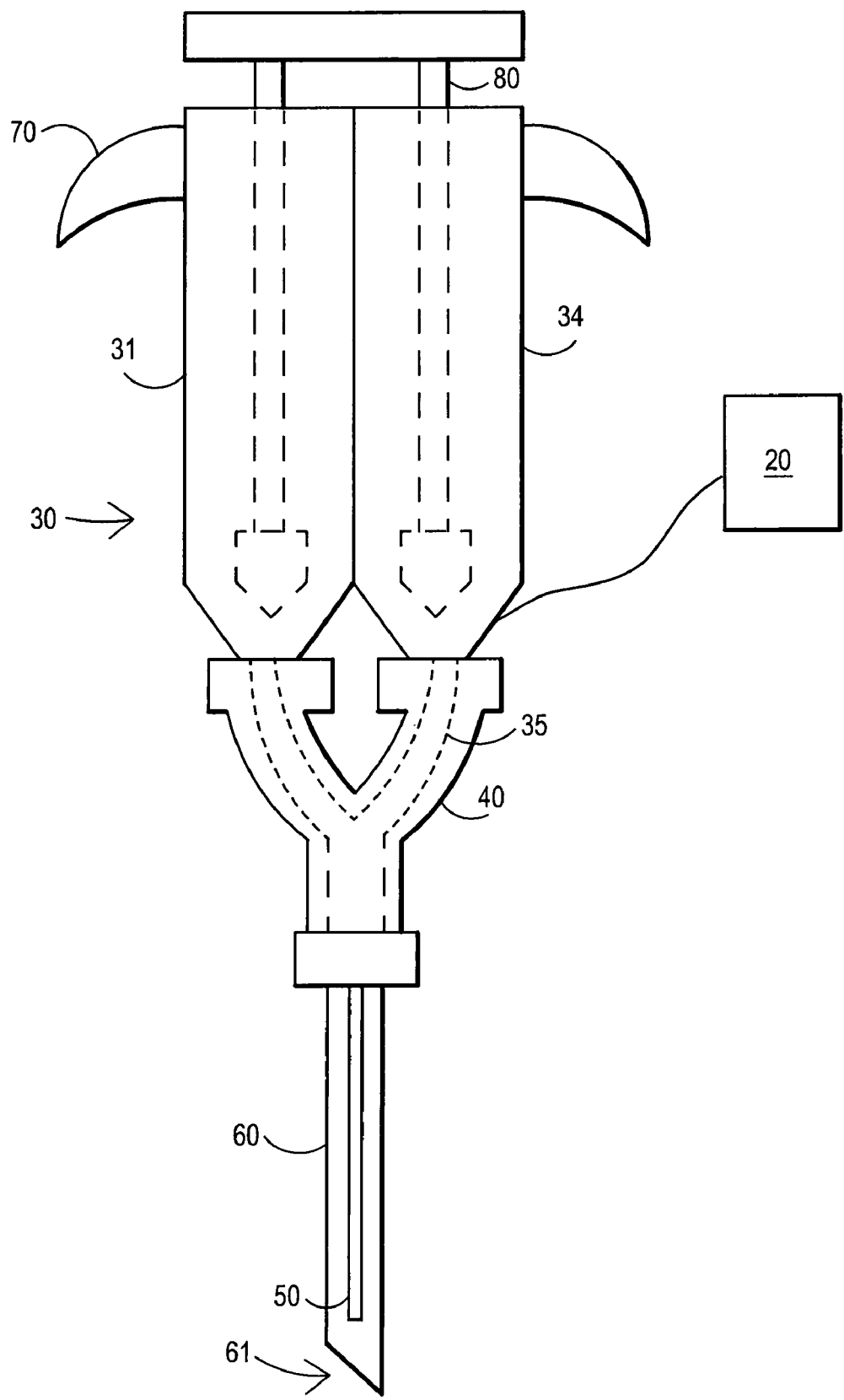

Various delivery devices can be used in the practice of this invention to introduce sealant into a disc such as illustrated in the figures, which are not intended to non-limiting as to type of devices that can be employed. For example, FIGS. 1A, 1B, and 1C illustrate representative devices of this invention that have been fully assembled. Each device is adapted for use to deliver fibrin sealant. In FIG. 1, the device 10 includes a pressure monitor 20, fluid reservoirs (such as a multi-barrel syringe) 30, a connector 40, a fluid delivery tube 50, and an introducer needle 60. The syringe, connector, and needle can be coupled using standard luer fittings. The fluid reservoirs can include handles 70 and plungers 80. Alternatively, the fluid reservoirs can be configured such that the reservoirs are flexible and can be squeezed or rolled to force fluids out. The introducer needle 60 can, for example, couple to the connector by a luer fitting at an end of the connector opposite to the end connected to the syringe. In FIG. 1, the fluid from barrel 31 is driven through a fluid delivery tube 50 that has been pushed through a plug 33 attached to or integral with the connector 40, with the fluid delivery tube being of sufficient length to be threaded into the introducer needle. Thus, in one embodiment, the fluid delivery tube 50 couples to a first barrel 31 of a multi-barrel syringe and the fluid delivery tube extends into the connector through a plug coupled to the connector. In one embodiment, the fluid delivery tube directly couples to the first barrel of the syringe, and the fluid delivery tube is affixed to the connector so that the fluid delivery tube cannot move within the introducer needle. Fluid from barrel 34 is pushed through a conduit 35 within the connector and flows into the introducer needle. Thus, the connector is adapted for conveying fluid from the fluid delivery tube into the introducer needle. The connector can include a passage 35 for fluid from the second barrel to the introducer needle, with the passage being of a diameter such that the fluid from the second syringe barrel is of a volume approximately equal to the volume of fluid delivered through the fluid delivery tube. In one embodiment, the fluid delivery tube is of a length such that it does not protrude out the end of the introducer needle. The fluids from barrel 31 and 34 mix near the distal tip 61 of the introducer needle 60. The pressure monitor 20 couples to barrel 31 via line 21 that is attached to a transducer such that the transducer of the pressure monitor is within the barrel to measure internal pressure within the barrel. The pressure measured within the barrel will be the same or nearly the same pressure as that at the distal tip of the introducer needle during a procedure. Thus, the pressure monitor allows the pressure within the disc to be monitored. In one embodiment, the multi-barrel syringe 30 has two barrels. Each barrel can be configured to couple to the connector or fluid delivery tube by a luer fitting. A delivery device of this invention may be equipped with a trip switch if a given pressure is reached, which reduces the chance of an over-pressurized disc.

Pressure monitors are available commercially. For example, a suitable pressure monitor is currently available from Merit Medical Systems, Inc. (Utah, US) sold as a Meritrans™ transducer. Other representative pressure monitors are disclosed in, for example, US patent application number 2005/0004518, incorporated herein by reference. In the device disclosed in 2005/0004518, a pressure transducer is integrally mounted in the plunger of a syringe under the plunger tip such that the force applied by the plunger to the fluid in the syringe is transmitted to the transducer and the resulting electronic signal is converted to a display value, aiding the physician in diagnosing diseased disks in the back. The transducer of the pressure monitor can be positioned in the barrel of a syringe or, alternatively, in the connector (or "hub").

The device depicted in FIG. 1B is similar to the device in FIG. 1A except that in FIG. 1B the fluid delivery tube 50 is integral with the connector so that the fluid delivery tube does not need to be inserted through a plug. The fluid delivery tube can be bonded to the connector or can be otherwise coupled to the connector so that fluid from the barrel flows into the fluid delivery tube. It should be appreciated that a first fluid, such as fibrinogen, is injected through either the fluid delivery tube 50 or through the conduit 35, with the activating compound being injected through the opposite passage from that used by the fibrinogen. Thus the two fluids flow through the device in coaxially and do not touch or mix until the given fluid exits the fluid delivery tube 50. Line "a" points to an alternative location for the transducer of the pressure monitor.

FIG. 1C depicts device 10 that includes a pressure monitor 20, a reservoir which in this case is a multi-barrel syringe 30, a Y-connector 40, a fluid delivery tube 50, and an introducer needle 60. In this embodiment, barrel 31 and barrel 34 are coupled to the Y-connector 40 such as through luer fittings. Fluid from barrels 31 and 34 flow into the Y-connector where mixing begins. The fluids then enter the fluid delivery tube 50, which extends into the introducer needle 60. The introducer needle 60 couples to the connector 40 via a luer fitting. In this embodiment, the pressure monitor is coupled to barrel 34 (the transducer is within barrel 34).

It should be appreciated that a wide variety of designs can be used for the fluid delivery device. For example, the device can include a delivery gun equipped with a ratcheting lever to make injection easier. Such a delivery gun could also be automated so that physical pressure is not needed by the physician in order for injection to proceed. It is envisioned that if such a delivery gun was used, the gun could be loaded with the multiple barrels that contain the fibrinogen and activating compound liquids. Compression of the lever would force plungers to push the fluids from out of the barrels and into the connector, fluid delivery tube, and/or introducer needle. Alternatively, the gun could use a screw-type action to move the plungers. Either embodiment gives the physician a mechanical advantage when injecting the components. What is important, however, is that in this invention the pressure monitor is always coupled to the delivery device.

Figure 2:
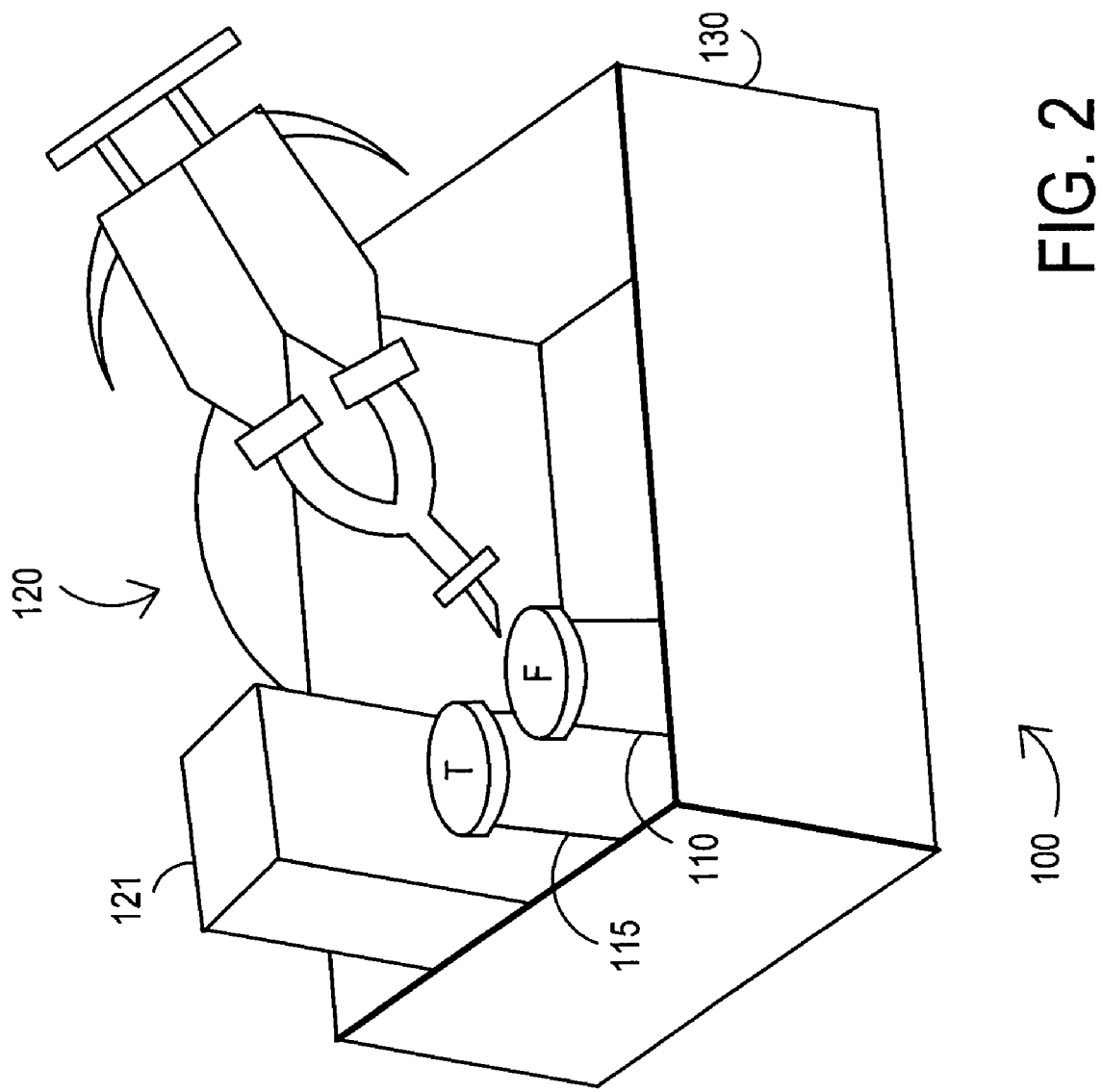
FIG. 2 shows another representative apparatus of this invention that includes an integrated coaxial flow connector ("hub").

FIG. 2 shows a representative kit of this invention. The kit 100 includes fibrinogen 110, an activating compound 115, and a fibrin sealant delivery apparatus 120 for injecting fibrin sealant into a human disc, wherein the apparatus is equipped with a pressure monitor 121. The kit may be stored and shipped in a suitable container 130. The kit may include additional items, such as but not limited to one or more additives, a source of calcium ions, a device for reconstituting freeze-dried fibrinogen, additional fluid delivery tubes, additional introducer needles, and so on.

Figure 3B:
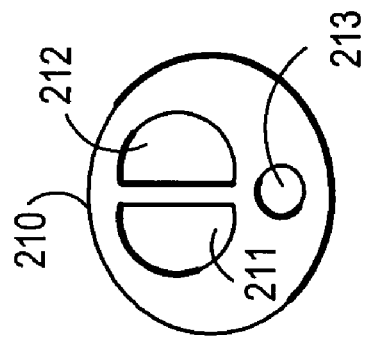
FIGS. 3A, 3B, and 3C show representative cross-sectional views of multi-lumen catheters.
Figure 3C:
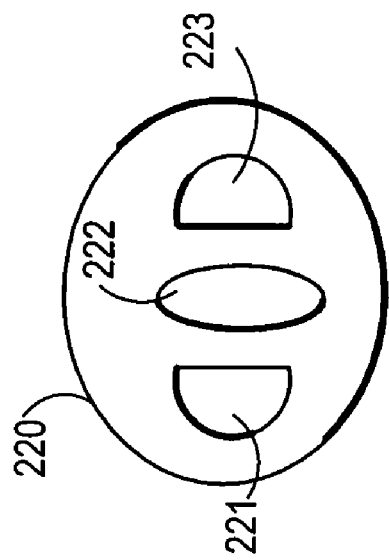
Figure 3A:
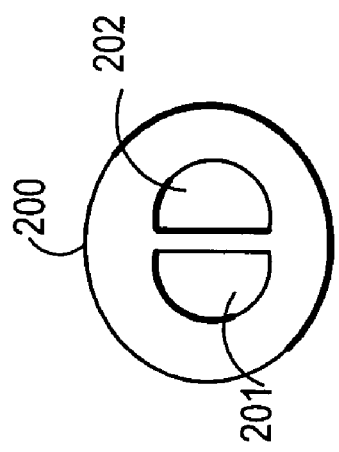

FIGS. 3A and 3B show representative cross-sectional views of multi-lumen catheters. FIG. 3A shows a bilumen catheter 200 wherein the lumen are in side-by-side arrangement and in which fibrinogen would be injected through lumen 201 and the activating compound through lumen 202. In FIG. 3B a trilumen catheter 210 is depicted wherein a first lumen 211 may carry one fluid, second lumen 212 carries a second fluid, and a third lumen 213 may carry an additive or have a wire inserted through the lumen 213 to improve the physical integrity and rigidity of a polymeric catheter. FIG. 3C depicts a trilumen catheter 220 wherein the lumen 221, 222, and 223 are arranged in sequence (in side-by-side relationship). A multi-lumen catheter can be used in this invention. A multi-lumen catheter can have a number of cross-sectional structures. The catheter can also have more than three lumen.

Referring now to FIG. 4, a representative delivery device of this invention is depicted. The device 310 includes a housing 320 that holds or is connected to some of the device's parts. The housing can be made from a variety of materials, but is typically made from one or more plastic materials. The housing can generally be referred to as being in the shape of a pistol, including a handle 321 and barrel 322. At least two reservoirs (cartridge) 330 is positioned within the barrel 322. The housing is adapted to receive and house the cartridge. The cartridge 330 is thus positioned within the barrel 322. The housing can be a multi-piece component, such as a two piece housing that is assembled using screws, or configured using snap-in type functionality. The specific design shown in FIG. 4 is merely representative and not intended to limit the types of housings employed in the practice of this invention.

In addition, a trigger 340 is operably connected to and situated within the housing so that the trigger 340 can slide from a first position into the housing to a second position as pressure is applied by the operator to the trigger 340. The housing 320 can include an internal stop, not shown, for the travel of the trigger 340.

Figure 5:
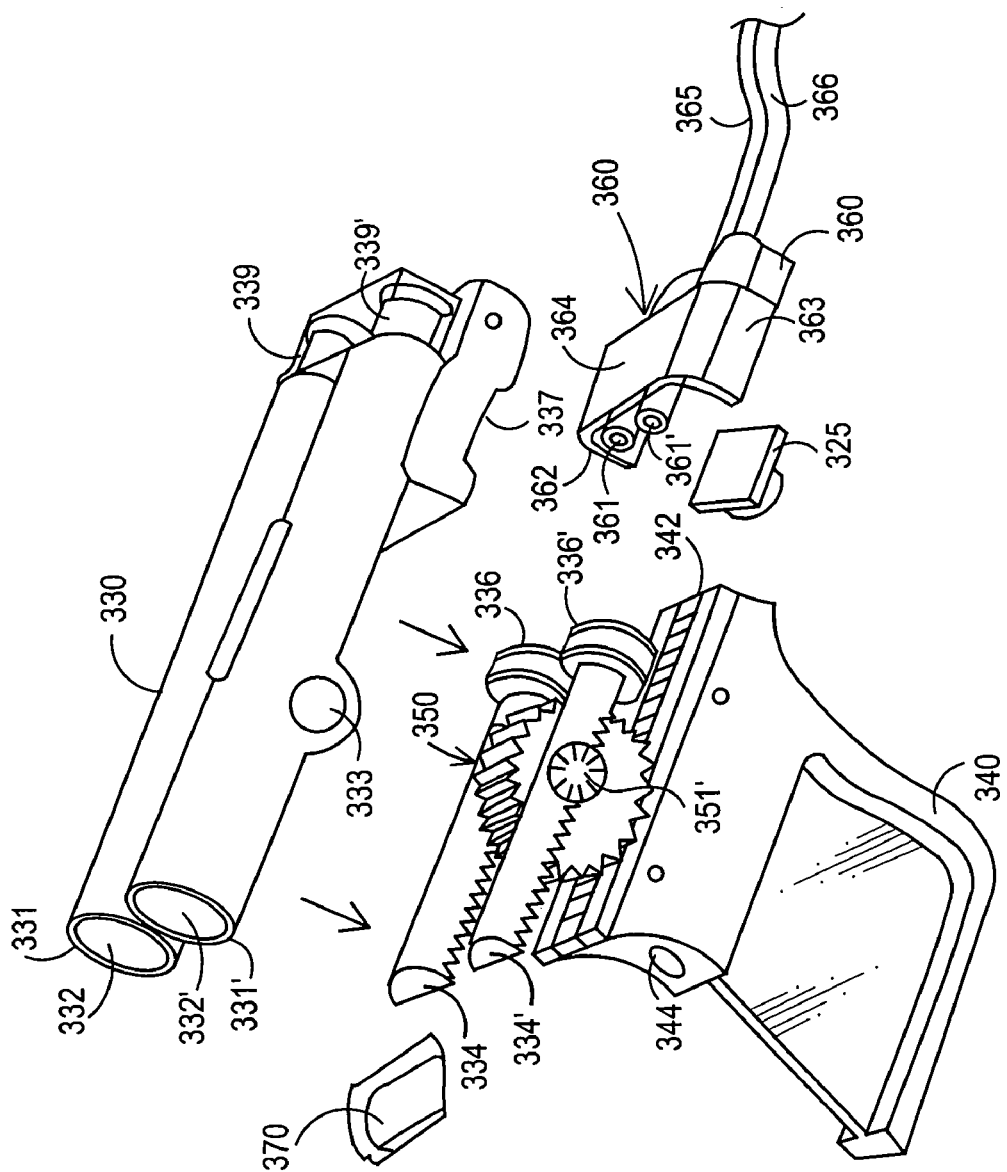
FIG. 5 shows a semi-exploded view of components of one embodiment of the device of this invention.
Figure 6:
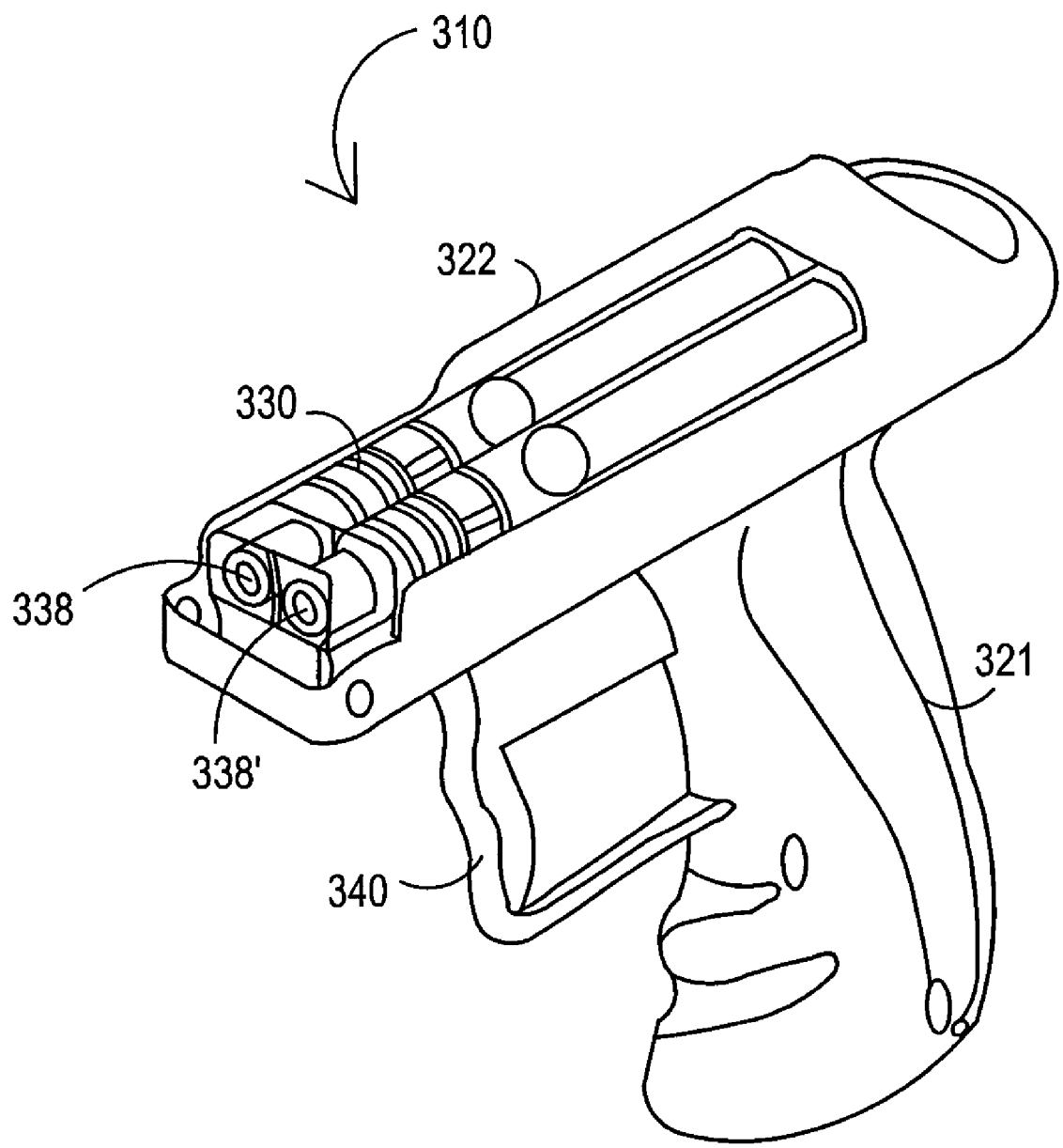
FIG. 6 shows a device of this invention, including exit ports 338, 338' of the cartridge 30.
Figure 7:
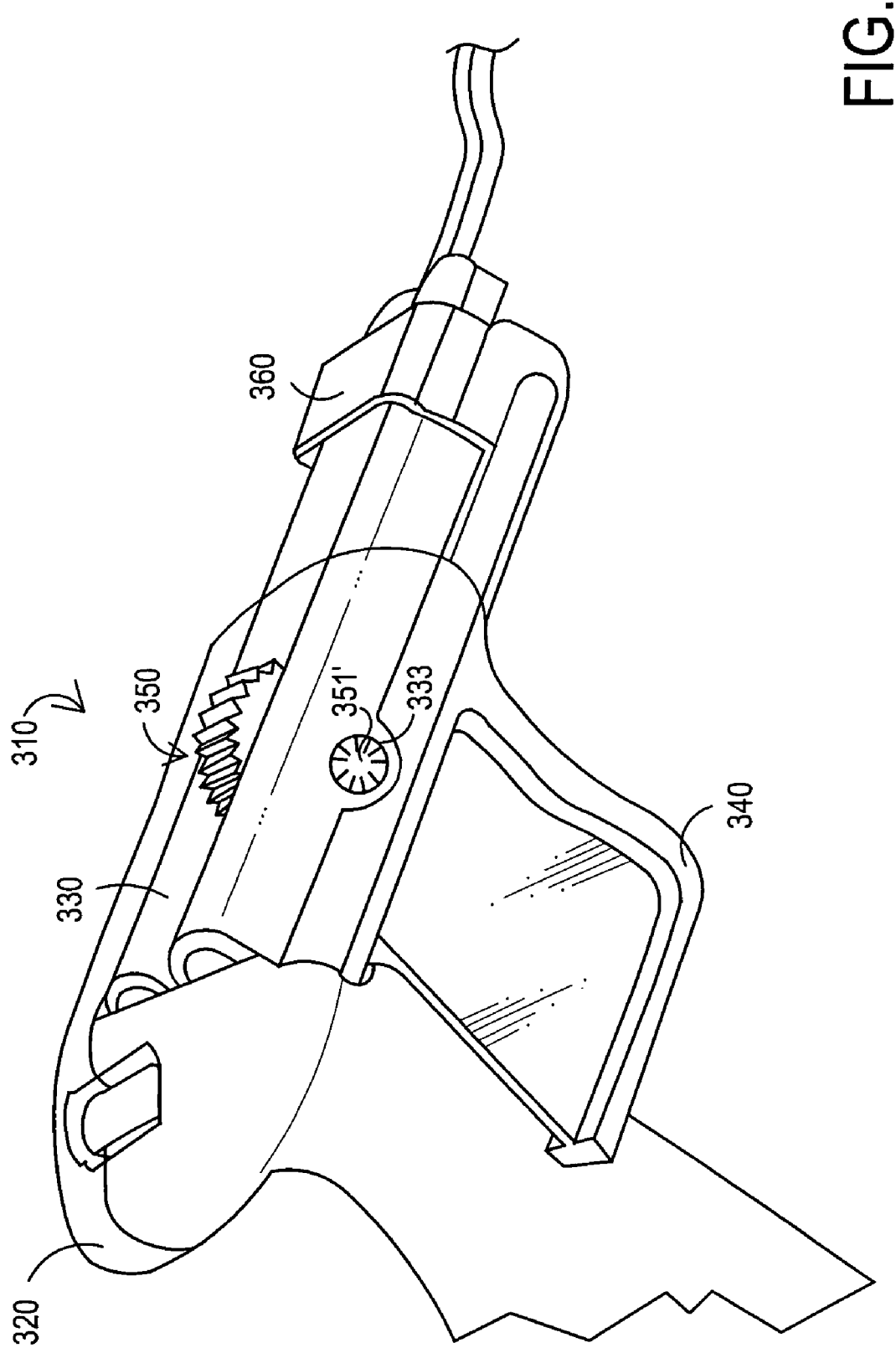
FIG. 7 shows a perspective view of the device of this invention.
Figure 8:
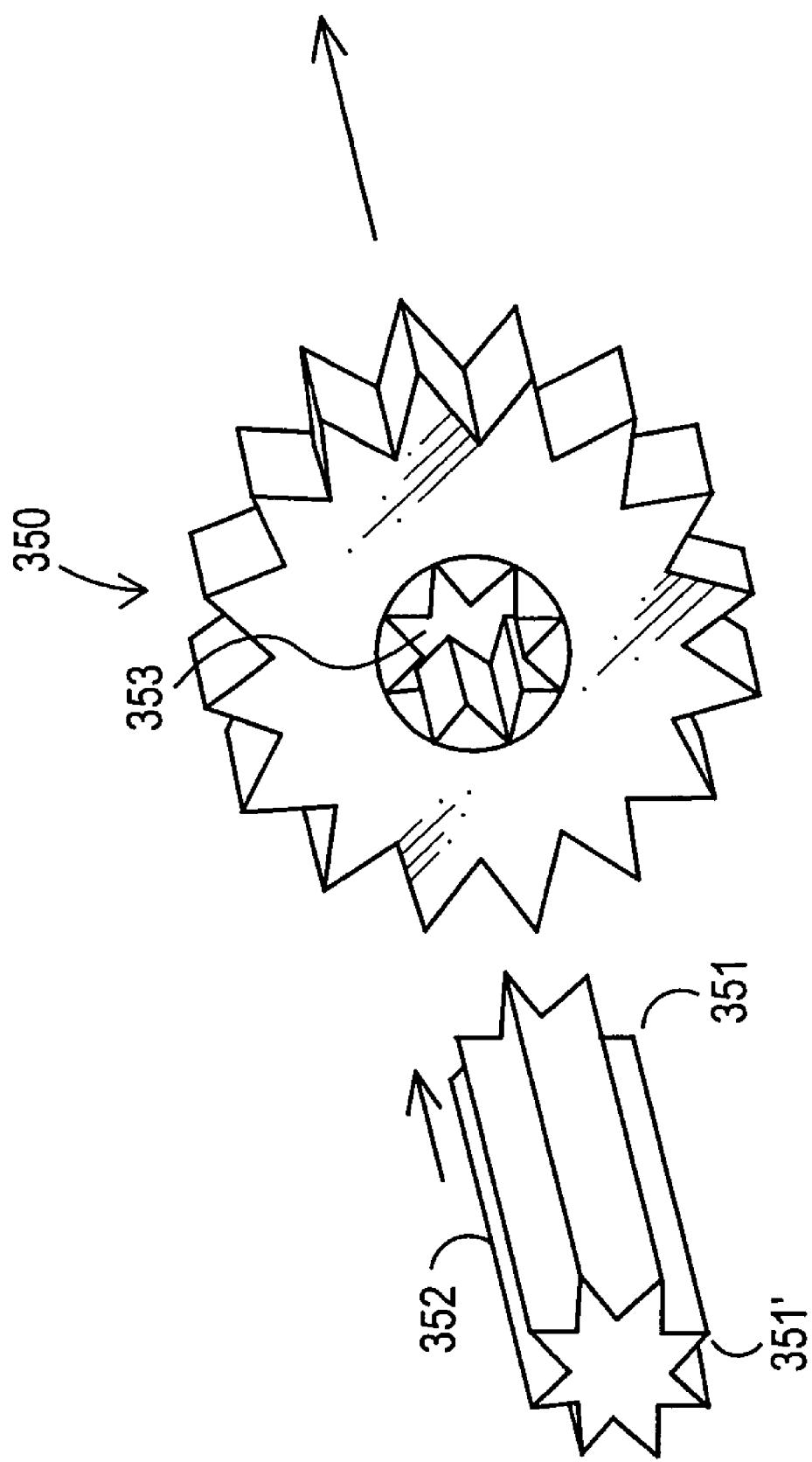
FIG. 8 shows a wheel assembly used in one embodiment of the device of this invention.

The cartridge 330 is depicted in greater detail in FIG. 5. Thus, the cartridge 330 includes two cylinders 331, 331' that each has a bore 332, 332' for receipt of a fluid. Each cylinder 331, 331' defines a generally straight tube having the same diameter for the length of the bores 332, 332'. The cartridge 330 may include one or more fittings, slots, or the like that serve to secure the cartridge 330 within the housing. For example in FIG. 5 the housing includes a fitting 353 that is configured to fit within slot 337 of the cartridge to thereby secure cartridge 330 from lateral movement. It should be appreciated that the cartridge 330 does not move upon application of pressure to the trigger 340. Rather, application of pressure to the trigger 340 engages the rack 342, wheel assembly 350, and rams 334, 334' to push the plungers 336, 336' toward the exit ports 338, 338' (see FIG. 6) of the cartridge 330. In FIG. 8, the extended gear ends 351, 351' of the wheel assembly 350 fit into bore 333 of the cartridge 330 (see also FIG. 7). It should be appreciated that the cartridge 330 can be integral with the housing 320. That is, the cartridge 330 need not be a separate and/or detachable component that is placed within the housing but instead can be formed as part of the housing during fabrication of the housing.

It should be appreciated that the wheel assembly 350 can be a single piece or can be assembled from multiple parts to form the assembly. Thus, for example, with respect to a multiple-part assembly, as depicted in FIG. 8, a toothed internal gear 352 having extended gear ends 351, 351' is inserted into internal bore 353 of wheel 350. The gear 352 is adapted to engage the wheel 350, such as by interdigitating teeth, so that the assembly would move as a single part during use of the device 310. In this embodiment, the inner toothed gear 352 can be seen to be sandwiched between the extended gear ends 351, 351'. Alternatively, the wheel assembly can be cast, forged, milled, or otherwise formed to manufacture a single monolithic wheel assembly. Alternatively to teeth, the wheel assembly 350, rack 342, and rams can be made of materials that engage with sufficient friction to provide the desired movement, using for example tacky rubber materials, materials have a grainy surface (e.g., with a sand-paper like finish), and so on.

Referring again to FIG. 5, there is shown a pressure readout display 370 that provides the surgeon with a pressure reading within one of the bores 332, 332' of the cartridge 330. A transducer, not shown, is configured to measure pressure within a bore and a line, not shown, from the transducer to the display 370 provides a signal to electronic circuitry that processes the signal and provides a reading to display 370. Thus, the pressure monitor couples to the delivery device through a line connected to a transducer in, for example, one of the syringes. Alternatively, the transducer can be located within the connector, or anywhere else where the transducer can be introduced within the device such that pressure of within the device can be measured. Preferably, the transducer is in the bore. The display can be but is not limited to an LCD.

Pressure monitors are available commercially. For example, a suitable pressure monitor is currently available from Merit Medical Systems, Inc. (Utah, US) sold as a Meritrans™ transducer. Other representative pressure monitors are disclosed in, for example, US patent application number 2005/0004518, incorporated herein by reference. In the device disclosed in 2005/0004518, a pressure transducer is integrally mounted in the plunger of a syringe under the plunger tip such that the force applied by the plunger to the fluid in the syringe is transmitted to the transducer and the resulting electronic signal is converted to a display value, aiding the physician in diagnosing diseased disks in the back. The transducer of the pressure monitor can be positioned in the barrel of a syringe or, alternatively, in the connector (or "hub").

A dispenser manifold 360 is shown in FIGS. 4 and 5. The dispenser manifold 360 includes dispenser manifold inlet ports 361, 361' that sealably align and couple with the exit ports 338, 338' of the cartridge 330. The dispenser manifold 360 is adapted to couple to the manifold coupling portion 339 of the cartridge using, for example, fittings 362, 363 that engage complimentary slots 339' so as to lock in the dispenser manifold 360 to the coupling portions 339, 339'. In the embodiment depicted in the FIGS, the exit ports 338, 338' are embodied within manifold coupling portion 339, 339'. The dispenser manifold 360 depicted in FIGS. 4 and 5 also includes an optional hood 364. The dispenser manifold 360 includes fluid tubes 365, 366 that receive and transfer fluid from the cartridge 330 to the needle assembly 380 which is depicted for example in FIGS. 9-11. The tubes 365, 366 can be made of a variety of materials, but in general are made of flexible materials to facilitate improved usage by the surgeon. Typically the tubes 365, 366 are made of polymeric materials, especially medical grade materials. Alternatively, the tubes can be made of soft metals or other materials that permit the tubes to flex. Thus the delivery manifold for delivering the fluids can include a delivery adapter that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to delivery fluid from one conduit to an inner needle and wherein the luer fitting is configured to delivery fluid from the second conduit to a space defined by the exterior of the inner needle and by a second larger diameter needle that connects to the luer fitting with the inner needle being within the insider of the larger diameter needle. FIG. 12 illustrates the device 310 where the manifold 360 has been operably connected to the housing 320 so that the inlet ports of the manifold 360 align with the exit ports of the cartridge 330.

Figure 13:
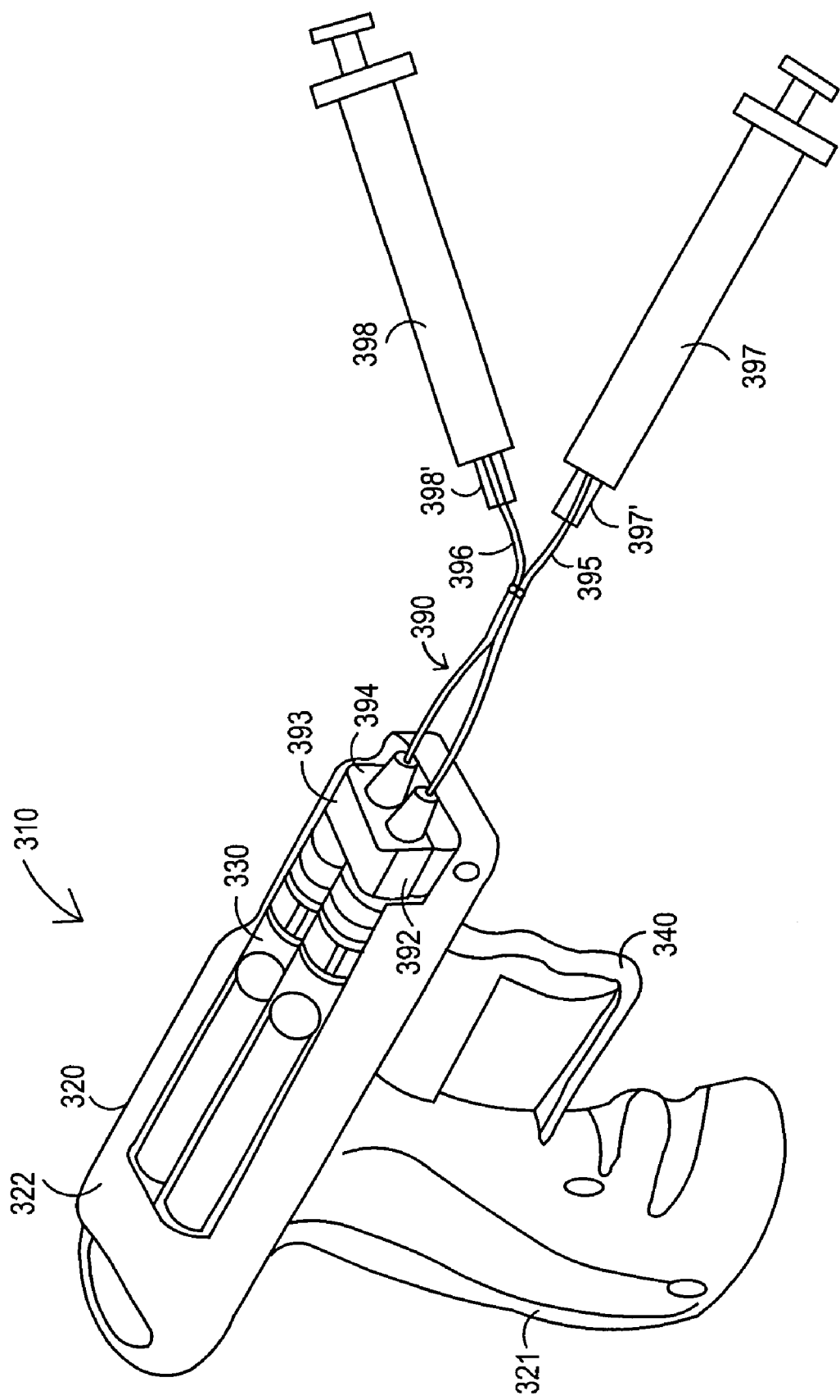
FIG. 13 shows the device of this invention with a fill manifold operably attached to the device.

Instead of the dispenser manifold 360, a fluid fill manifold 390 as depicted in FIG. 13 can be used to load fluids into the cylinders 331, 331' of the cartridge 330. Like the dispenser manifold 360, the fill manifold 390 includes inlet ports (not shown) that sealably align and couple with exit ports 338, 338'. The fill manifold 390 includes fittings 392, 393, and an optional hood 394. However, the fill manifold 390 includes tubes 395, 396 that couple to syringes 397, 398 that are filled with the fluids to be introduced into the cylinders 331, 331'. The syringes 397, 398 connect via luer fittings 397', 398' to the tubes. Thus during use the syringes 397, 398 are filled with fluids (e.g. a thrombin solution and a fibrinogen solution) to be introduced into the cylinders 331, 331'. The syringes are locked into place using the luer fittings, and then the fluids are injected into the cylinders at which time the plungers 336, 336' are driven back. Next, the fill manifold 390 is removed and replaced with the dispenser manifold 360 after which time the surgeon injects the biologic sealant of choice into a desired location, such as a disc, in the body. Thus, the fill manifold for introducing fluids into the cylinder includes a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor. It should be appreciated that the fill manifold 390 can be alternatively connected to a wide variety of refilling parts other than the syringes 397, 398. Thus, the fluid fill manifold 390 can use, for example, pressurized containers, automated injection devices, fluid bags that are manually or automatically squeezed to effect refilling into the cylinders, fluid ampoules that are punctured with needles to access the fluids using pressurized gas to force the fluids into the cylinders, and so on.

Figure 11:
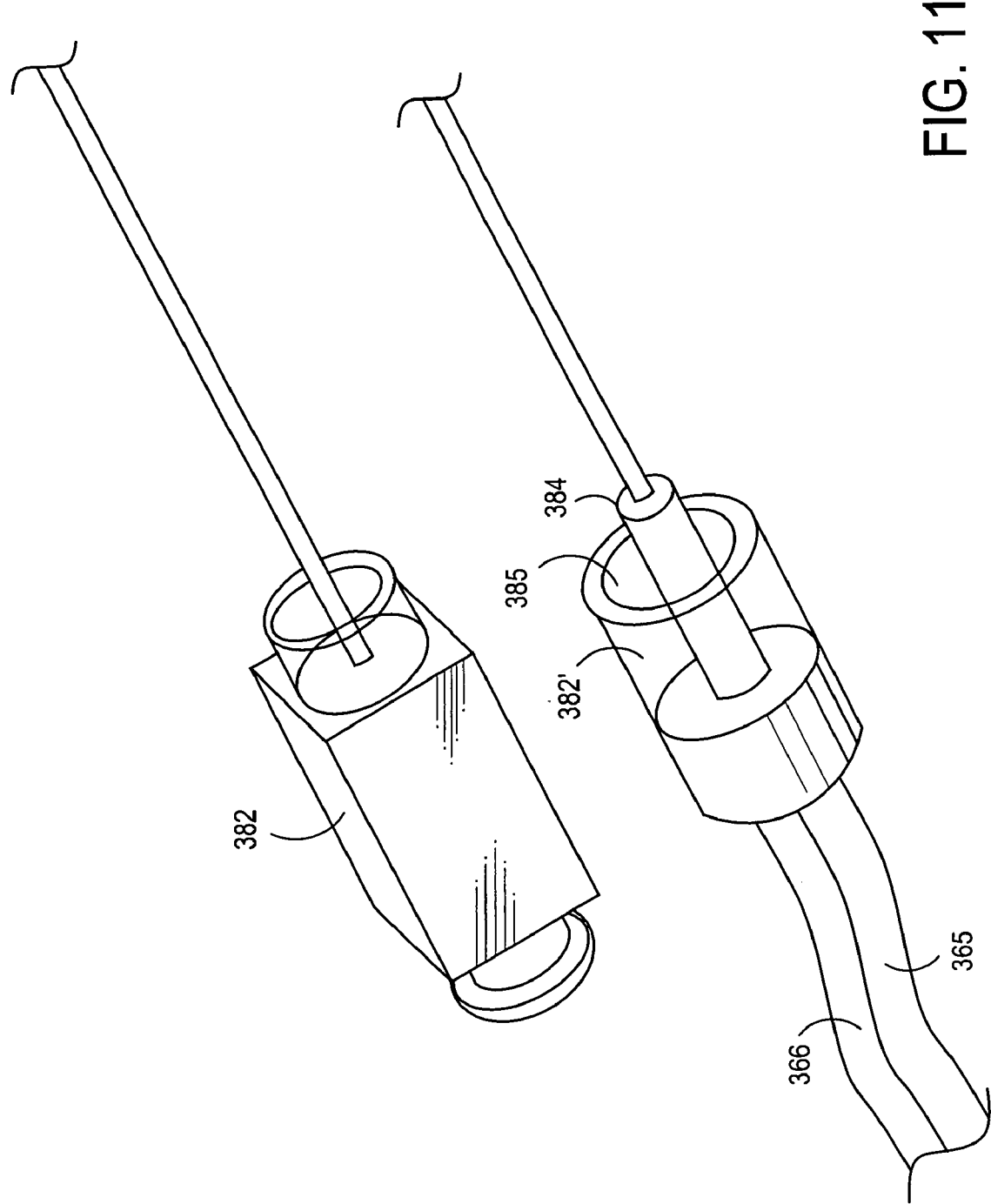
Figure 12:
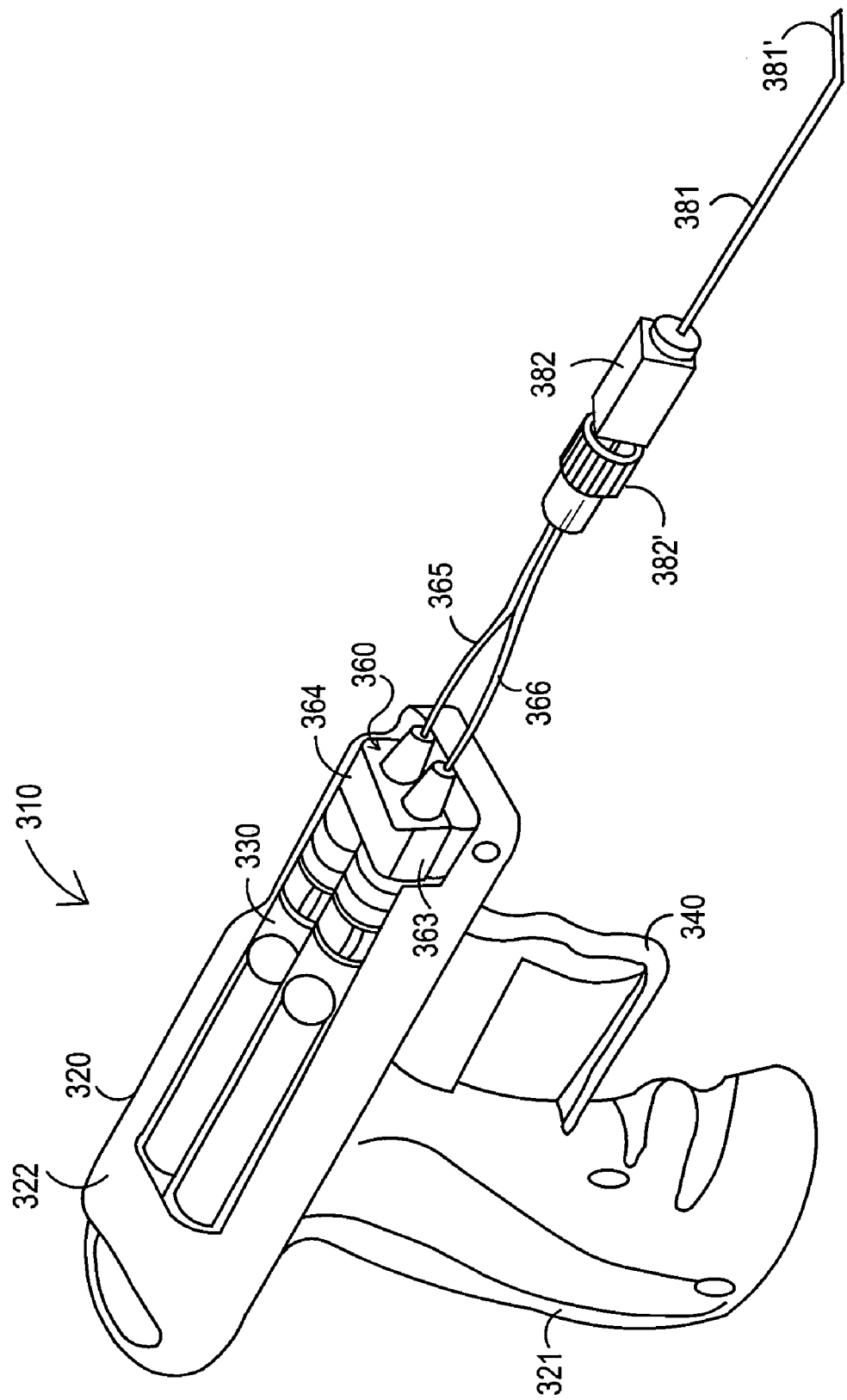
FIG. 12 shows the device of this invention with a delivery manifold operably attached to the device.

The needle assembly 380 is depicted in FIGS. 9-11. The needle assembly may include two coaxial needles, or an outer needle and an inner polymeric catheter. In FIG. 9, the outer needle 381, which is inserted directly into the patient to be treated, is connected via luer fittings 382, 382' with the outer needle 381 surrounding an inner needle 383 (see FIG. 10). The outer needle is typically an 18-22 gauge spinal needle that includes a bent portion 381' to assist the surgeon in navigating the body during insertion of the spinal needle. The inner needle can be of any size such that fluids may flow in the gap between the needles. In certain embodiments, the inner needle 383 may include ports near the tip 383' to facilitate potentially improved mixing of the fluids. Likewise, the tip 383' may be capped. FIGS. 3A-3C illustrate cross-sectional views of needles and catheters that may be employed in the practice of this invention. If a multi-lumen catheter or needle is employed, then the luer fitting would be adapted to delivery each fluid to a respective lumen. Referring again to FIGS. 9-11, the inner needle 383 can be of any length but typically is sized so that when the inner and outer needles are coupled together the tip 383' of the inner needle 383 extends to within between 1 mm and 50 mm of the tip 381' of the outer needle 381. In one embodiment, a fibrinogen solution is provided to the inner needle 383 while a thrombin solution is provided to the outer needle 381. Fluid mixing is initiated at the tip 383' of inner needle 383.

FIG. 11 shows a detailed embodiment of the luer fitting 382'. Thus, fibrinogen tube 365 feeds fibrinogen solution directly into a port 384 that couples to the inner needle 383. By contrast, tube 364 feeds thrombin solution, for example, into the hub (the void space) 385 of the luer fitting 382' whereby when the outer needle 381 is connected via luer fitting 382 the thrombin solution flows into the hub and into needle 381. The two fluids do not commingle until one of the solutions exits the inner needle 383.

Figure 14:
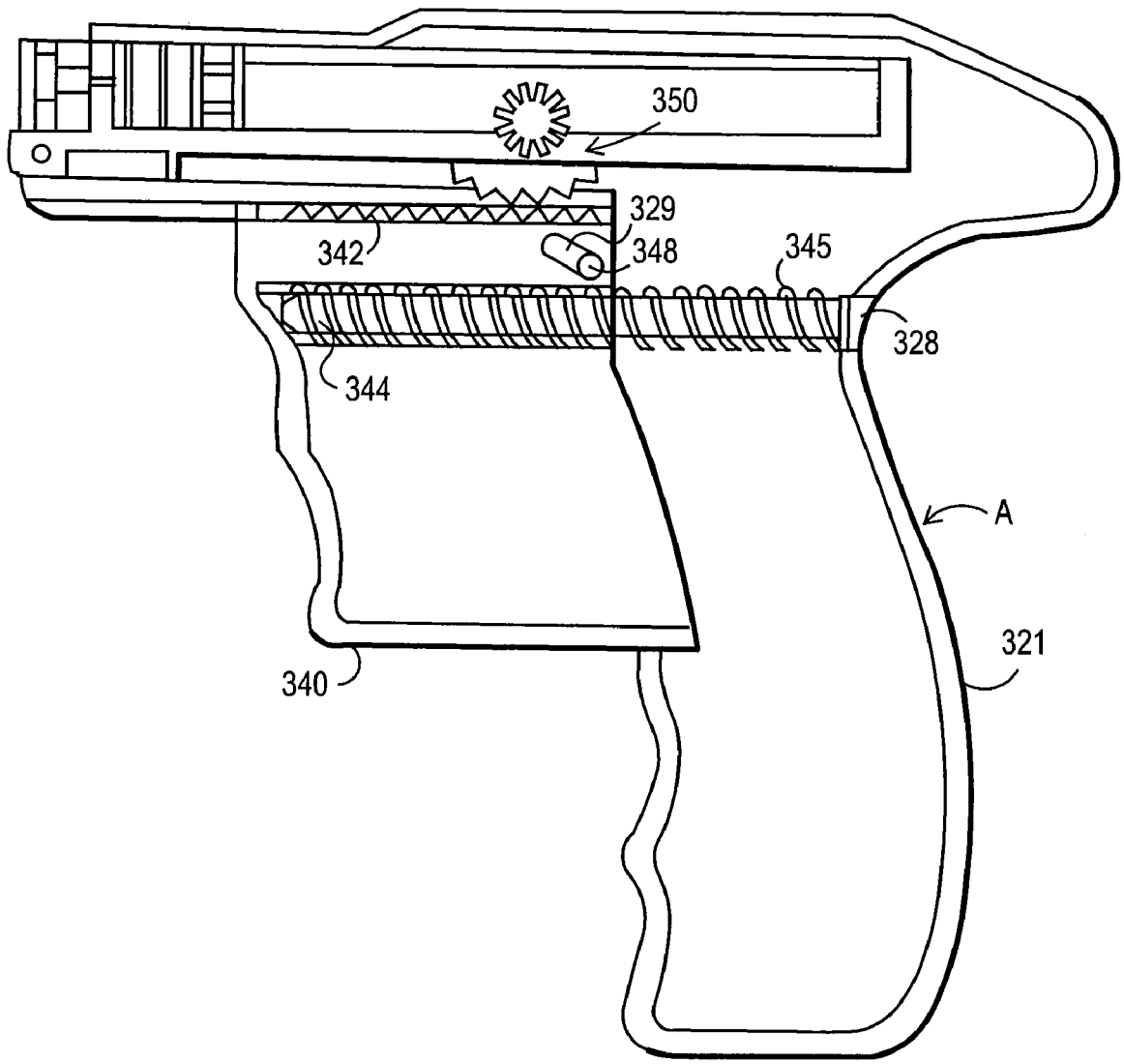
FIG. 14 shows the device of this invention from a cross-sectional view.

The trigger 340 is depicted in greater detail in FIG. 5. The trigger includes a toothed rack 342. Upon application of pressure by the surgeon to the trigger 340, the trigger 340 and rack 342 move backwards in the direction of the handle 321. The rack 342 then engages the wheel assembly 350, which rotates as the rack 342 moves backward. The wheel assembly 350 thereby drives rams 334, 334' which move plungers 336, 336' forward toward the exit ports 338, 338'. In one embodiment, the trigger is configured such that the teeth of rack 342 engage the teeth of the wheel assembly 350 when pressure is applied to the trigger 340, and configured such that the rack 342 drops away when pressure is released so that the respective teeth no longer engage. This configuration can be provided, for example, by adapting the housing 320 and trigger 340 such that the backward motion of the trigger raises the rack 342 such as, for example, in FIG. 14. In FIG. 14, the trigger 340 includes a guide bore 344 wherein a guide post 328 attached to the housing glides through the guide bore 344 upon application of pressure to the trigger 340. Upon release of pressure, spring 345 returns the trigger 340 to its original position. As the trigger 340 slides towards side A of the handle 321, a pin 348 that is mounted or integral with the rack 342 slides in the slot 329 to force the rack 342 up or down depending on the angle of the slot 329 to thereby engage the wheel assembly 350 as pressure is applied to the trigger 340. In this configuration, the slot 329 is a part of and integral with the housing 320. Alternatively, the rack 342 may include a slot with a pin being mounted within the housing 320, such that the pin glides in the slot to force the rack 342 to engage the wheel assembly 350.

Figure 15:
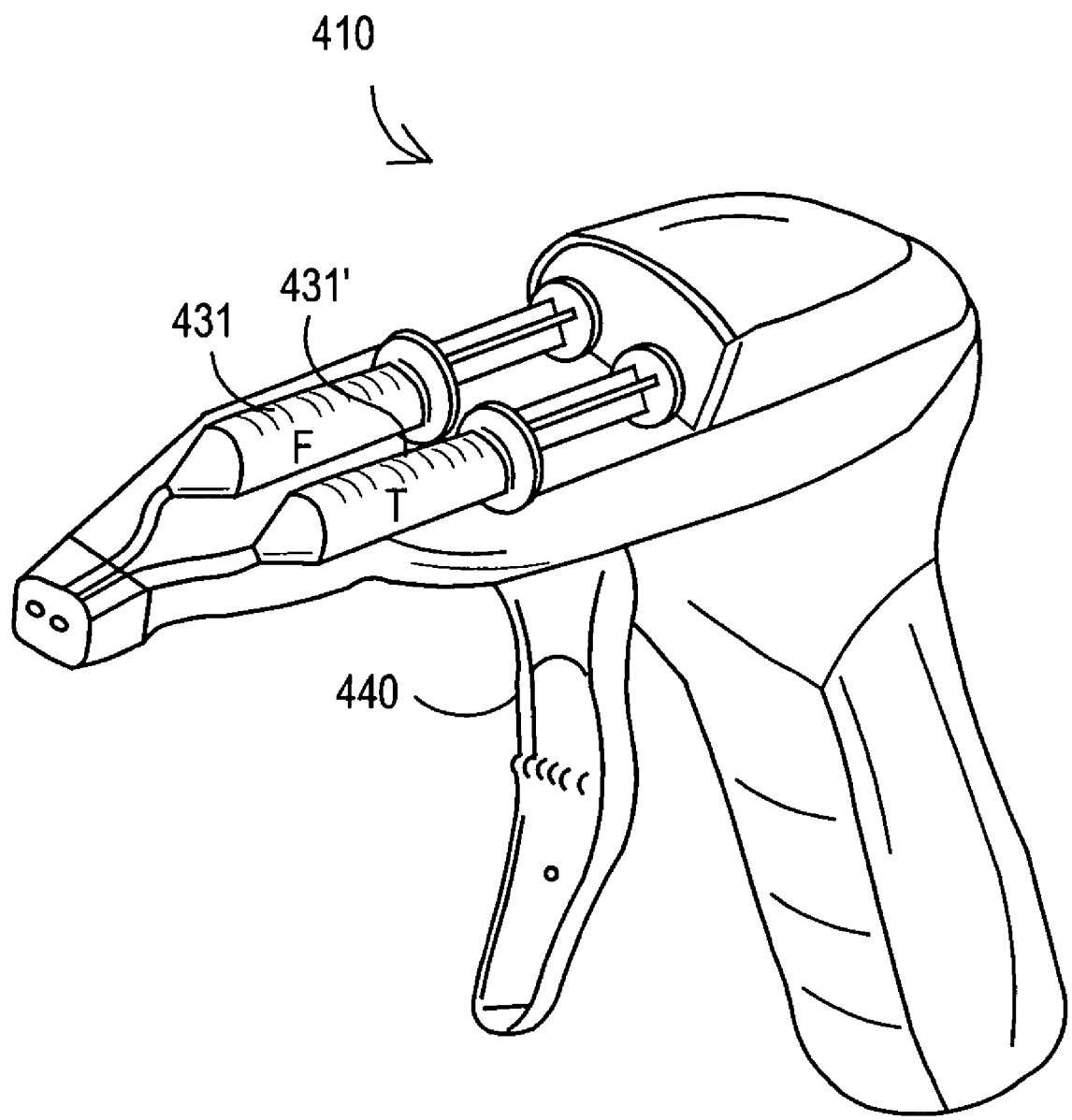
FIG. 15 shows another embodiment of the apparatus of this invention.

FIG. 15 depicts another embodiment of the delivery device of this invention. In FIG. 15, a delivery device 410 is depicted having a different trigger configuration than in, for example, FIG. 4. In FIG. 15, the trigger 440 pivots around a pin, for example, whereby force is applied to the rams to drive the fluid out of the cylinders 431, 431'. One to four squeeze repetitions may be needed to deliver, for example, 4 mL of total fluid. This and other embodiments of this invention can be configured to be force limiting, such as a 100 pounds per square inch maximum and/or 10 pounds per square inch of maximum trigger force. In one embodiment, the ratchet that drives the fluids out of the device will only click once per squeeze, using either locking or non-locking motion. A spring, not shown, returns trigger 440 to its starting position prior to the next squeeze repetition. In this embodiment, the drive system may be the same or different than the wheel assembly 350 discussed above.

Figure 16:
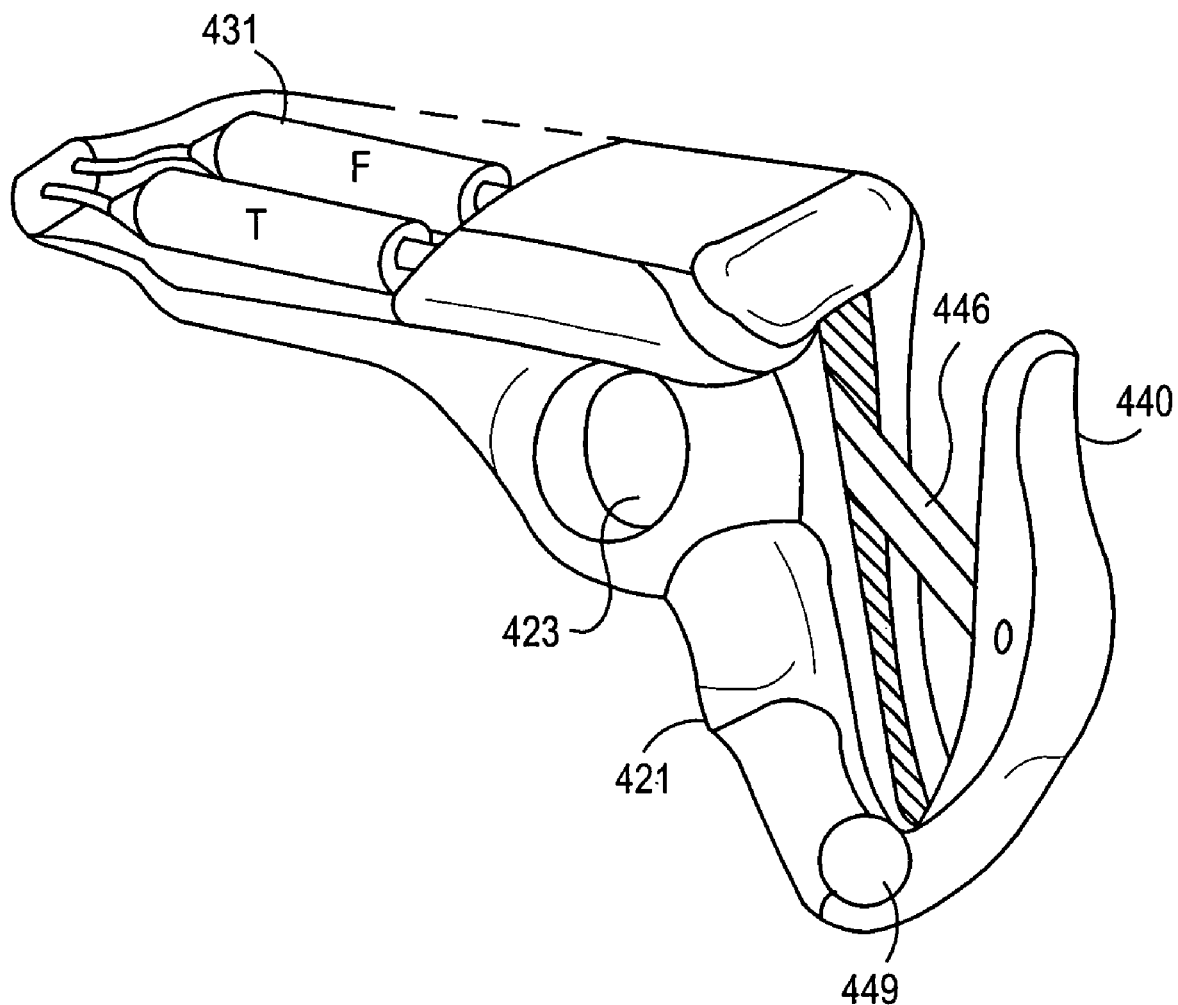
FIGS. 16 and 16A show another embodiment of the apparatus of this invention.
Figure 16A:
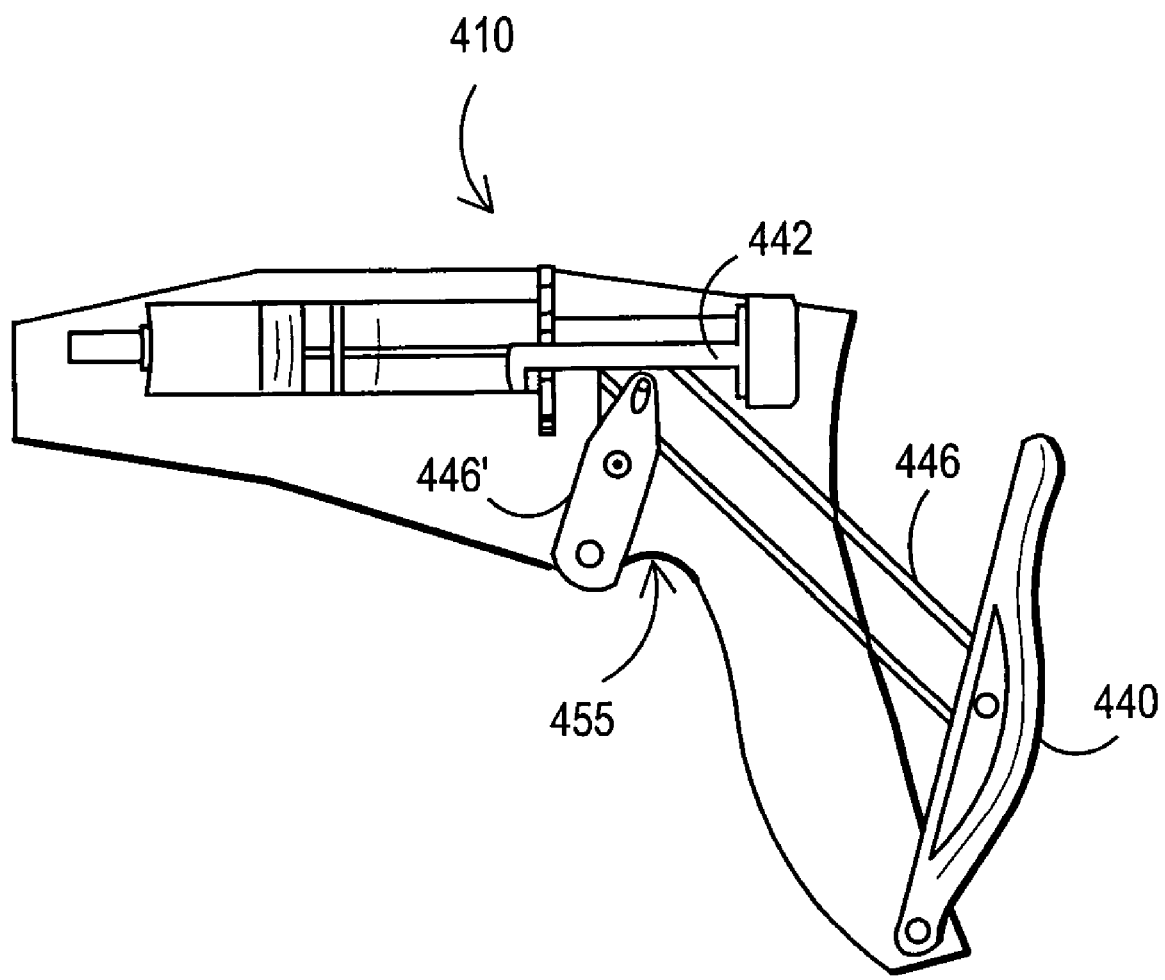

FIG. 16 depicts another embodiment of the invention where the trigger is squeezed on the opposite side of the handle 421 to the fluid reservoirs. In this configuration, the trigger 440 attaches to the handle 421 at pivot point 449. The trigger 440 engages the drive system through drive rod 446. An optional hole 423 is included as part of the housing and handle for placement of at least one finger by the surgeon. In this configuration, the trigger 440 is actuated by direct pressure from the surgeon's palm. The drive assembly can be constructed as in FIG. 16A where application of pressure to the trigger 440 causes the rod 446 to engage a rack 442. The rod 446 can be guided by ratchet arm 446', which may be part of the drive assembly.

Figure 17:
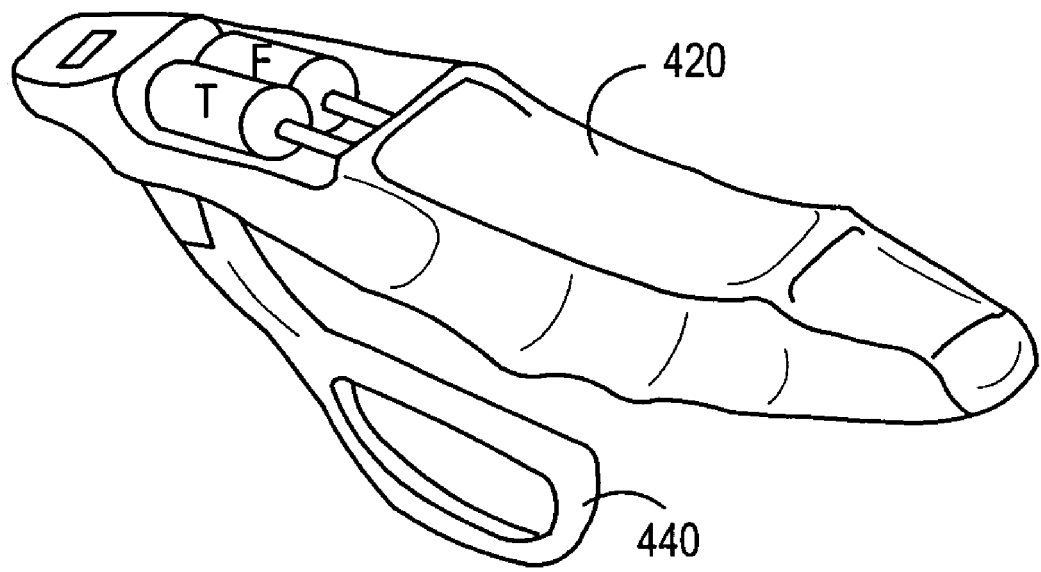
FIGS. 17 and 17A show another embodiment of the apparatus of this invention.
Figure 17A:
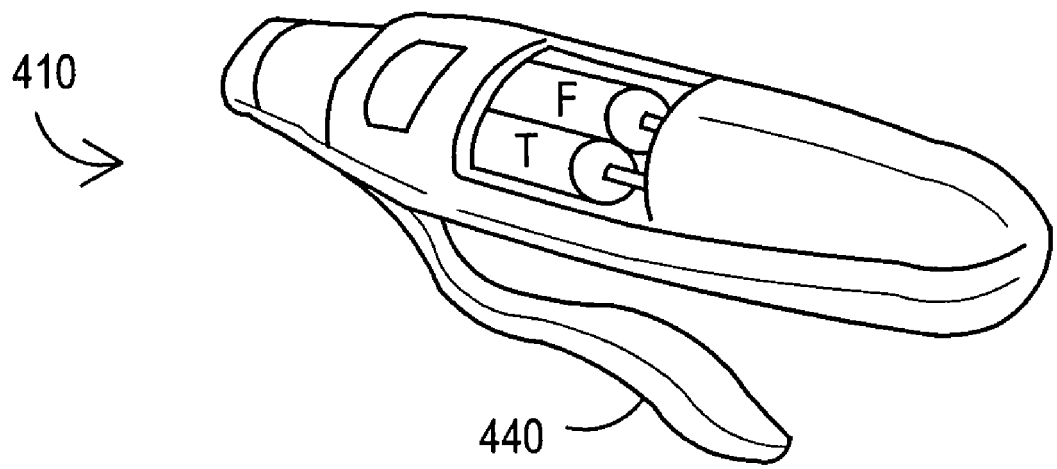

In FIG. 17, device 410 includes an inclined finger loop as the trigger 440. Application of pressure by the surgeon by squeezing the trigger forces the trigger 440 to move toward the housing 420 whereby the drive assembly, not shown, dispenses fluids from the reservoirs. Alternatively, as depicted in FIG. 17A, the trigger does not include a loop.

Figure 18:
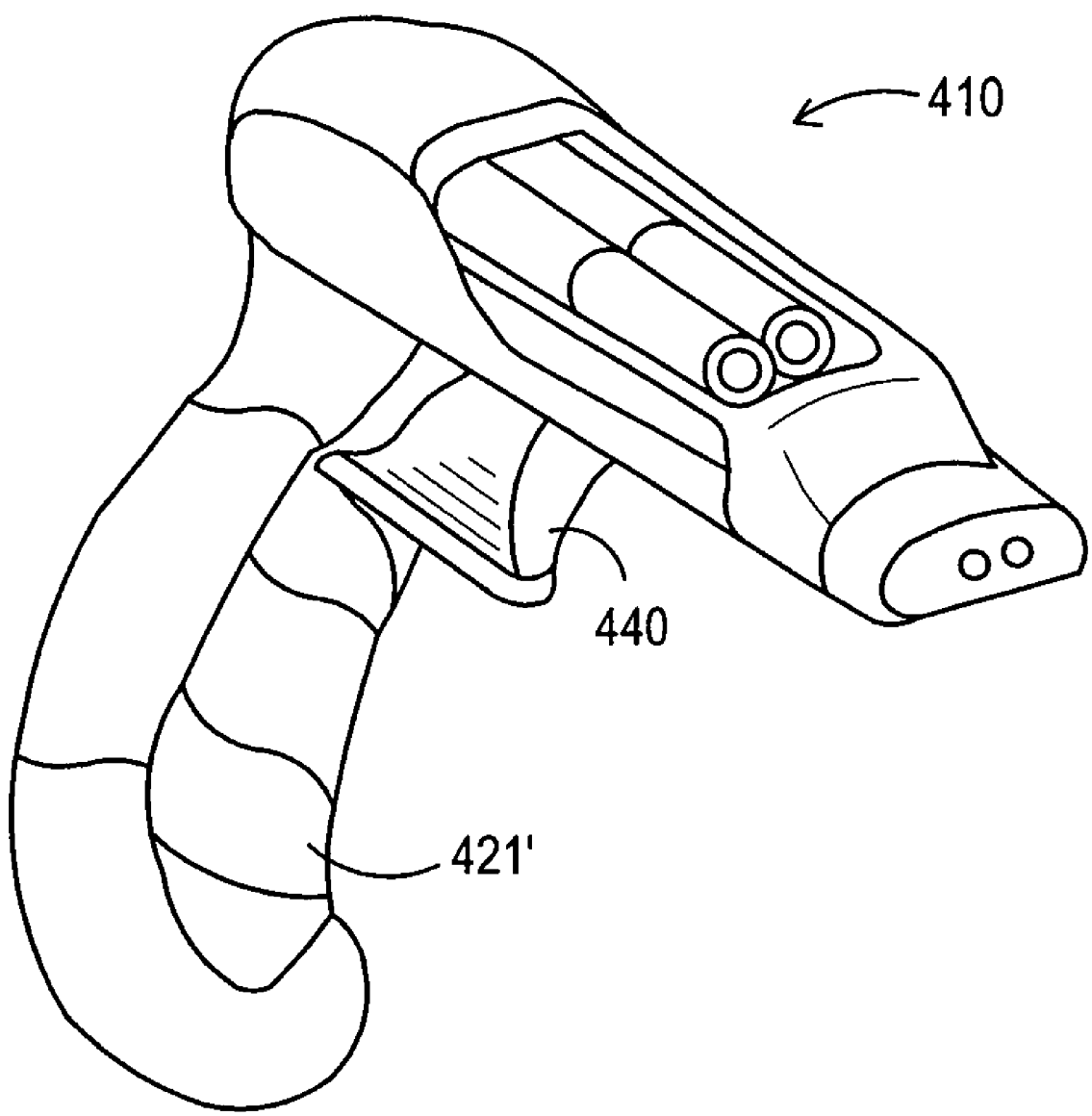
FIG. 18 shows another embodiment of the apparatus of this invention.

In FIG. 18, device 410 includes a soft grip 421' that can be formed from a variety of elastomeric materials or foam. In this configuration, the trigger 440 can be sized for from 1 to 4 finger operation. If desired, a soft grip could provide the surgeon with improved grip or comfort when depressing the trigger. Similarly, the handle can include hatching, ridges, or other the like to improve the grip of the device in the surgeon's hand.

FIGS. 19A and 19B show alternative drive assemblies for use in the practice of this invention. Thus, in FIG. 19A a drive assembly 455 is configured such that the trigger 440 moves through a pivot point that results in the plungers 436, 436' are advanced by application of pressure from the advance rod 456. By contrast, in FIG. 19B the drive assembly is driven by the trigger 440 such that a rod 456 causes a gear 457 to engage a rack 442 to drive the plungers 436, 436'. FIG. 19C illustrates a similar configuration to that in FIG. 19B with an alternative engagement of the trigger 440 to the gear 457.

FIG. 20 illustrates a basic ratcheting design where the trigger 440 moves the plunger 436 through a rack (not shown) that engages the plunger 436 as pressure is applied to the trigger 440 by a surgeon by squeezing the trigger. In this configuration, a single repetition will push one-half of the fluid volume out of the reservoirs at the end of the stroke.

Figure 21A:
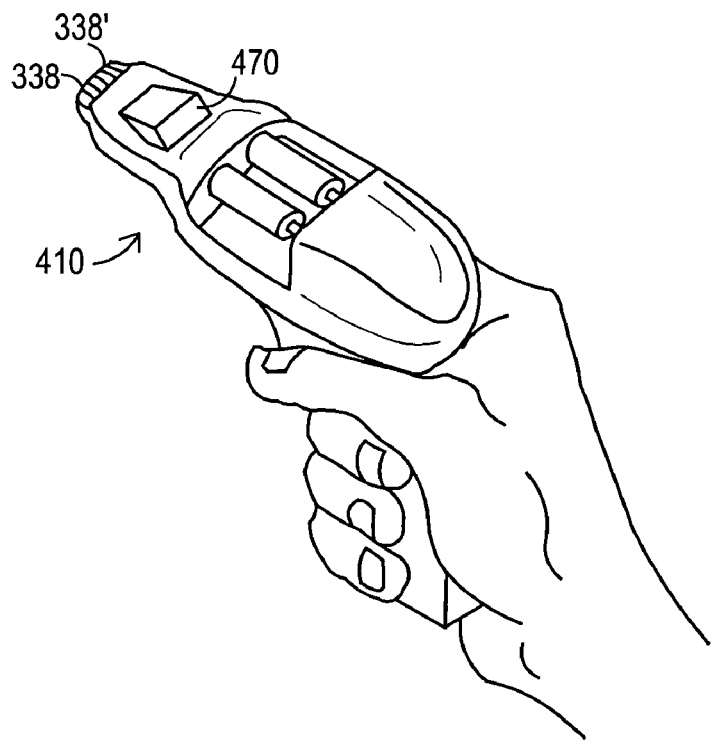
FIGS. 21A-21B show additional embodiments of the pressure display configuration locations.
Figure 21B:
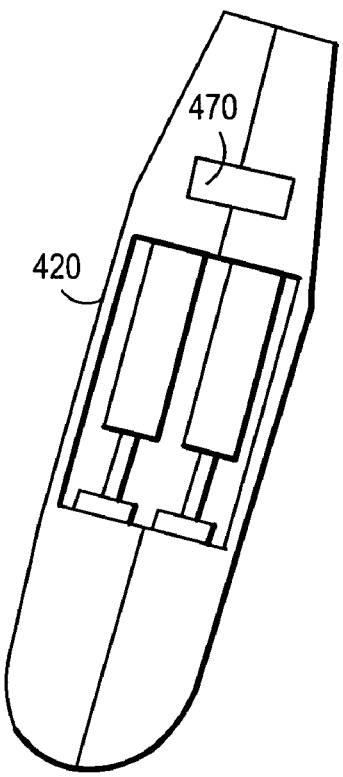

In FIG. 21A an alternative embodiment of the device 410 is shown in which the pressure display is positioned at the front of the device, near the exit ports 38, 38'. In FIG. 21A the display 470 has a raised profile whereas in FIG. 21B the display 470 is mounted flush to the housing 420.

Figure 22B:
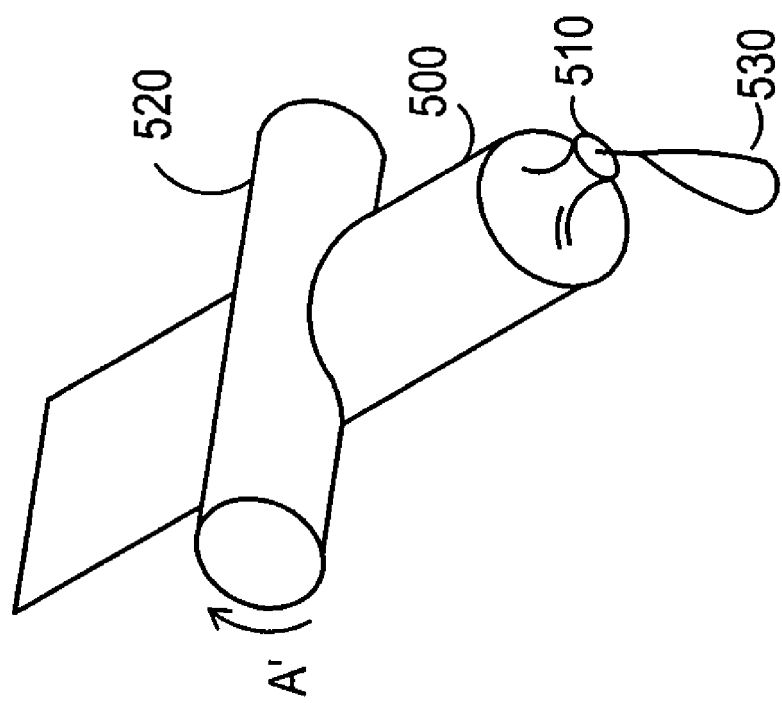
FIGS. 22A and 22B illustrate an alternative embodiment of the fluid delivery reservoirs of this invention.
Figure 22A:
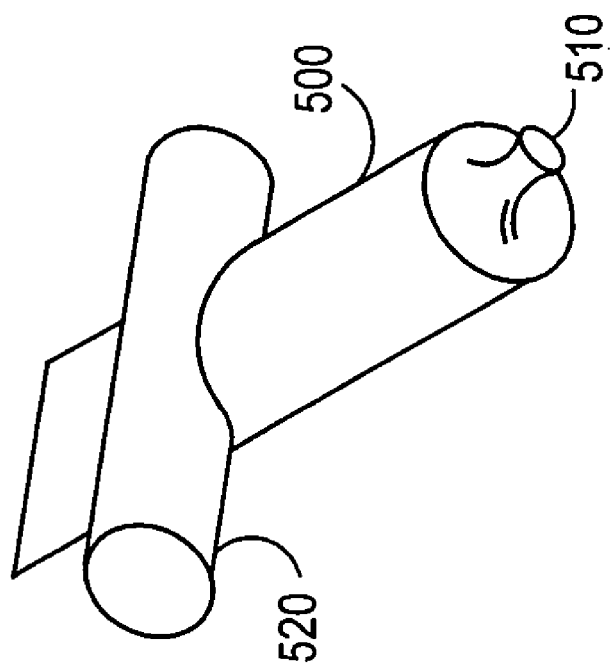

FIGS. 22A and 22B illustrate an alternative embodiment of the fluid delivery reservoirs of this invention. In the embodiment as shown in FIG. 22A the reservoir 500 holds sealant or a component of a sealant. The reservoir includes an exit port 510 for the sealant. A roller 520 It should be appreciated that the roller 520 shown in FIG. 22A is illustrative and can be of a variety of structures that allow application of pressure so that sealant flows from the reservoir 500. For example, the roller 520 could also be in the form of a pair of rollers, or could be a flat structure that simply presses straight down on the reservoir 500. Of course, the device for application of pressure (roller 520 in FIG. 2822A) could also be angled or of any configuration that facilitates sealant to be ejected from the reservoir 500. As shown in FIG. 22B, when the roller 520 is rolled in the A' direction, pressure is applied to squeeze sealant 530 out of the reservoir.

The following Examples are provided to describe and illustrate the practice of the invention and not to limit or to restrict the scope of the invention. It will be apparent to those skilled in the art that certain changes and modifications may be practiced within the scope of the present invention.

The following protocols, materials and procedures may be partly modifications of procedures and adaptations of materials reported in U.S. Pat. Nos. 5,324,775, 5,328,955, 5,626, 863, 5,324,775; 5,328,966; and 5,583,114. All of these references are incorporated herein by reference, respectively.

Example 1

A 105 mg/ml (10.5% W/V) aqueous solution of fibrillar collagen in 0.05 M sodium bicarbonate buffer and 0.15 M sodium chloride is adjusted to pH 9.5. 2.5 ml of this biomaterial solution (solution A) is aspirated into a dual chamber polypropylene cartridge through one of the two extrusion flanges of the cartridge. 2.5 ml of a solution of difunctionally activated N-succinimidyl carbonate PEG (DSC-PEG, MW 3600) in 0.005 M sodium carbonate/bicarbonate buffer and 0.15 M sodium chloride at pH 6.0 and in a 1 to 10 molar ratio of collagen (solution A) to DSG-PEG (solution B) is filled into the second chamber of the cartridge.

Both chambers of the cartridge are closed by attaching a spiral mixer nozzle (3.2 mm inner diameter, 6.2 cm length, 0.38 ml void volume) onto the dual extrusion flanges. The cartridge is placed into a manual application instrument that allows for a reproducible and volume controlled extrusion of the bio-material in increments of 0.5 ml per step. A blunt tip aspiration needle (18 gauge, 90 mm length) is placed on the tip of the mixer nozzle. Immediately prior to this application of the sealant, the handle of the application instrument is pressed three times (3.times.0.5 ml) in order to fill the void of the mixer and needle with the mixed bio-material precursor solutions. About 1 ml of mixed precursor solution flows out of the needle tip and is discarded. The cross linking process is now activated and care must be taken to apply the sealant without delay, i.e. within less than about 60 seconds in this Example.

A bovine cadaveric lumbar trunc is placed in prone position (spine axis horizontally with spinal processes facing up). An introducer needle is inserted through an annulus pulposus. All of this is done prior to activating the crosslinking process. A needle fitted to a sealant applicator is inserted into the introducer needle. About 1-2 ml of sealant is injected into the disc by pressing the handle of the application instrument. The needles are then withdrawn from the incision and the sealant allowed to cure.

Example 2

A 380 mg/ml (38% w/v) aqueous solution of human serum albumin (MW 68000) in 0.1 M sodium bicarbonate buffer and 0.15 M sodium chloride is adjusted to pH 8.2 (solution A buffered protein solution). A 200 mg/ml (25% w/v) aqueous solution of difunctionally activated N-succinimidyl propionate PEG (DSP-PEG, MW 3400) in 0.01 M sodium carbonate/bicarbonate buffer at pH 6.0 is prepared as solution B (cross linking agent). Solutions A and B are placed in the dual chamber cartridge and injected as described in Example 1. In this Example 2, the application of the sealant without delay is particularly important because of the short curing time of this type of sealant (2-3 minutes).

Example 3

180 mg/ml (18% w/v) of PEG tetraacrylate (MW 8200) is dissolved in a buffer of 0.02 M sodium phosphate at pH 7.4 and 0.15 M sodium chloride. Ammonium persulfate (0.01 M) and sodium bisulfite (0.005 M) are added to the solution that now represents the polymerizable bio-material with thermal polymerization initiation system. 5 ml of this bio-material solution is aspirated into a polypropylene syringe that is fitted with a Luer type adapter tip. The syringe is closed by placing a temperature-controlled, flow through heating cylinder, that is connected to a control unit, onto the tip of the syringe. The syringe is placed into a manual application instrument that allows for a reproducible and volume-controlled extrusion of the bio-material in increments of 0.25 ml per step. A blunt tip aspiration needle (18 gauge, 90 mm) is placed on the tip of the heating cylinder. The handle of the application instrument is pressed four times (4×0.25 ml) in order to fill the void of the heating cylinder and needle with the bio-material solution. About 0.2 ml of bio-material solution flows out of the needle tip and is discarded. Immediately prior to the application of the sealant, the heater is turned on and the heater control unit is set at 50 C. As soon as the heater reaches a temperature of 45 C, the polymerization process will start and care must be taken to apply the sealant without delay, i.e. within less than about 15 seconds and at a rate of approximately two steps per minute (0.5 ml of volume/min). The sealant is injected as described in Example 1.

Example 4

Fluoroscopic Guided Intra-Discal Injection

After sterile preparation, an introducer needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. A contrast agent is injected to confirm needle placement. In patients with chemical radiculitis, the contrast agent can be observed to be leaking through the annular fissures and/or intra-discal pathology, thus permitting their identification. Once the needle is properly positioned in the intra-discal space, the curable composition (or its components) is injected using the syringe system of this invention having a pressure monitor. Pressure is monitored to ensure that the disc is not over-pressurized. The curable composition is observed to force the contrast agent from the intra-discal space as it seals the annual fissures. Alternatively, the contrast agent is injected with the curable composition. Alternatively, no contrast agent is used. The procedure seals the defects/fissures of the annulus fibrosus and stops the chemical leakage and facilitates regeneration within the disc.

It is envisioned that the present invention may be used to address various conditions through use of the in situ curable, bio-compatible polymerizable or polymeric material composition in a manner similar to that described in the examples above. Discussion of this invention referenced particular means, materials and embodiments elaborating limited application of the claimed invention. The invention is not limited to these particulars and applies to all equivalents. Although this invention has been described above with reference to particular means, materials and embodiments, it is to be understood that the invention is not limited to these disclosed particulars, but extends instead to all equivalents within the scope of the following claims.

What is claimed is:

1. A method of repairing a defect in an annulus fibrosus of an intervertebral disc, without excising the entire nucleus pulposus of the disc, comprising: inserting an introducer needle having a tip through the annulus fibrosus by puncturing the annulus fibrosus with the introducer needle so that the tip of the introducer needle is in the nucleus pulposus, then injecting an in situ curable, bio-compatible polymerizable or polymeric material composition that includes a cross-linking agent into the disc through the introducer needle directly or indirectly so that the in situ curable composition contacts a defect in the annulus fibrosus; and curing said material in situ, wherein the injection of the situ curable, bio-compatible polymerizable or polymeric material composition is performed using an apparatus for percutaneous delivery of a sealant comprising: at least two fluid reservoirs, the introducer needle having a distal tip that is in fluid communication with at least one reservoir, a fluid delivery tube that is in fluid communication with a second reservoir, wherein the fluid delivery tube has a tip and wherein the fluid delivery tube is configured so that the tip of the fluid delivery tube does not extend past the distal tip of the introducer needle during use.

2. A method as claimed in claim 1 wherein said curable material is in flowable liquid form.

3. A method as claimed in claim 1 wherein said curable material comprises a combination of at least two components, and wherein at least one of said components is a cross linkable material and at least one other of said components is a cross linking agent for said cross linkable material.

4. A method as claimed in claim 3 wherein said cross linking agent is a polymeric compound having at least two epoxy groups therein.

5. A method as claimed in claim 3 wherein said cross linking agent is a chemical cross linking agent that is reactive with said cross linkable material.

6. A method as claimed in claim 1 wherein said defect is an opening in said annulus fibrosus that has been caused surgically.

7. A method as claimed in claim 1 wherein said defect is an opening in said annulus fibrosus that has been caused by herniation.

8. A method as claimed in claim 1 wherein said defect is an opening in said annulus fibrosus that has been caused by trauma.

9. A method as claimed in claim 1 wherein said defect is an opening in said annulus fibrosus that has been caused by natural degeneration.

10. A method as claimed in claim 1 wherein said defect is an opening in said annulus fibrosus that has been caused by dehydration or loss of disc height due to dehydration.

11. A method as claimed in claim 1 wherein said curable material comprises at least one polymeric component.

12. A method as claimed in claim 1 wherein said curable material is cured in situ by the action of heat thereon.

13. A method as claimed in claim 1 wherein said curable material is cured in situ by the action of electromagnetic radiation thereon.

14. A method as claimed in claim 1 wherein said curable material is cured in situ by the action of UV light.

15. A method as claimed in claim 1 wherein said cross linkable material comprises a flowable, semi-solid material.

16. A method as claimed in claim 1 wherein said in situ cured material comprises a visco-elastic bio-compatible material that has physical properties that are at least substantially similar to the physical properties of said annulus fibrosus.

17. A method as claimed in claim 1 wherein said in situ curable material comprises a biological material.

18. A method as claimed in claim 1 wherein said in situ cured material is biodegradable over a period of time that is substantially equal to the period of time during which additional annulus fibrosus material grows to an extent sufficient to fill said defect.

19. A method as claimed in claim 1 wherein said in situ curing is accomplished in less than 2 hours.

20. A method as claimed in claim 1 wherein said in situ curing is accomplished in up to about 40 minutes.

21. A method as claimed in claim 1 wherein said in situ curing is accomplished after at least about 2 minutes.

22. A method as claimed in claim 1 wherein said in situ curing is accomplished after at least about 30 seconds.

23. A method as claimed in claim 1 wherein said cured material comprises a hydrogel.

24. A method as claimed in claim 1 wherein said defect in said annulus fibrosus comprises at least one fissure in the annulus fibrosus.

25. A method as claimed in claim 24 wherein said at least one fissure has been caused by disc degeneration.

26. A method according to claim 1, further comprising a pharmaceutically active agent selected from the group consisting of growth factors, differentiation factors, enzymes, receptor agonists or antagonists, antibodies, hormones, analgesics, local anesthetics, anti-inflammatory drugs, TNF-α inhibitors, anti-microbial agents; antibiotics; antiproliferative, cytotoxic, and antitumor drugs; antiangiogen; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics; analgesics; oncology agents; cardiovascular drugs; glycoproteins; fibronectin; peptides; interferons; cartilage inducing factors; protease inhibitors; vasoconstrictors, vasodilators, demineralized bone or bone morphogenetic proteins; hormones; lipids; carbohydrates; proteoglycans, versican, decorin, biglycan; antiangiogenins; antigens; DBM; hyaluronic acid and salts and derivatives thereof; polysaccharides; cellulose compounds; gene therapy reagents; genetically altered cells, stem cells; cell growth factors; type I and II collagen; collagen hydrolysate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; cartilage; oxygen-containing components; enzymes; melatonin; vitamins; nutrients, and combinations thereof.

27. A method as claimed in claim 1, wherein the apparatus for delivering a biocompatible sealant includes at least two reservoirs for fluids to be delivered, an actuation assembly that causes the fluids to flow out of the reservoir through an exit port in the reservoir, and a pressure monitor coupled to the delivery device to measure pressure within the device.

* * * * *